United States Patent
Pomper et al.

(10) Patent No.: US 10,156,521 B2
(45) Date of Patent: Dec. 18, 2018

(54) RED FLUORESCENT ALDEHYDE DEHYDROGENASE (ALDH) SUBSTRATE

(71) Applicant: THE JOHNS HOPKINS UNIVERSITY, Baltimore, MD (US)

(72) Inventors: Martin G. Pomper, Baltimore, MD (US); Haofan Wang, Rockville, MD (US); Il Minn, Ellicott City, MD (US); Steven D. Leach, Baltimore, MD (US); Ronnie C. Mease, Fairfax, VA (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 14/767,195

(22) PCT Filed: Feb. 21, 2014

(86) PCT No.: PCT/US2014/017735
§ 371 (c)(1),
(2) Date: Aug. 11, 2015

(87) PCT Pub. No.: WO2014/130834
PCT Pub. Date: Aug. 28, 2014

(65) Prior Publication Data
US 2015/0369738 A1 Dec. 24, 2015

Related U.S. Application Data

(60) Provisional application No. 61/767,576, filed on Feb. 21, 2013, provisional application No. 61/921,913, filed on Dec. 30, 2013.

(51) Int. Cl.
| | |
|---|---|
| G01N 21/64 | (2006.01) |
| C07D 207/44 | (2006.01) |
| C07F 5/02 | (2006.01) |

(52) U.S. Cl.
CPC ....... *G01N 21/6428* (2013.01); *C07D 207/44* (2013.01); *C07F 5/022* (2013.01); *G01N 21/6486* (2013.01); *G01N 2021/6439* (2013.01)

(58) Field of Classification Search
None
See application file for complete search history.

(56) References Cited

U.S. PATENT DOCUMENTS

| | | |
|---|---|---|
| 8,193,350 B2 | 6/2012 | Suzuki et al. |
| 8,277,775 B2 | 10/2012 | Bittman et al. |
| 2004/0248203 A1 | 12/2004 | Dratz et al. |
| 2010/0036133 A1 | 2/2010 | Dratz et al. |

OTHER PUBLICATIONS

Storms et al. "Isolation of primitive human hematopoietic progenitors on the basis of aldehyde dehydrogenase activity." Proceedings of the National Academy of Sciences 96(16): 9118-9123, 1999.*
Chapter 1: Fluorophores and their amine-reactive derivatives, Section 1.4, Molecular Probes Handbook: A guide to fluorescent probes and labeling technologies, 11th edition, 2010, available online from ThermoFisher Scientific, at thermodisher.com/probes.*
ATDBio "Bodipy dyes" available online at www.atdbio.com/content/41/BODIPY-dyes, copyright 2016.*
Armstrong, L.; Stojkovic, M.; Dimmick, I.; Ahmad, S.; Stojkovic, P.; Hole, N. & Lako, M. Phenotypic characterization of murine primitive hematopoietic progenitor cells isolated on basis of aldehyde dehydrogenase activity. Stem Cells 22, 1142-1151, doi:22/7/1142 [pii]10.1634/stemcells.2004-0170 (2004).
Balber, A. E. Concise review: aldehyde dehydrogenase bright stem and progenitor cell populations from normal tissues: characteristics, activities, and emerging uses in regenerative medicine. Stem Cells 29, 570-575, doi:10.1002/stem.613 (2011).
Bigas, A. & Espinosa, L. Hematopoietic stem cells: to be or Notch to be. Blood 119, 3226-3235, doi: blood-2011-10-355826 [pii]10.1182/blood-2011-10-355826 (2012).
Black, W. J.; Stagos, D.; Marchitti, S.A.; Nebert, D.W.; Tipton, K.F.; Bairoch, A. &Vasiliou, V.,*Human aldehyde dehydrogenase genes: alternatively spliced transcriptional variants and their suggested nomenclature. Pharmacogenet Genomics 19, 893-902, doi:10.1097/FPC.0b013e3283329023 (2009).
Bunting, K. D. ABC transporters as phenotypic markers and functional regulators of stem cells. Stem Cells 20, 11-20 (2002).
Cherry, A. B. C. & Daley, G. Q. Reprogrammed Cells for Disease Modeling and Regenerative Medicine. Annu Rev Med 64, 277-290, doi:DOI 10.1146/annurev-med-050311-163324 (2013).
Duncan, A. W.; Rattis, F.M.; DiMascio, L.N.; Congdon, K.L.; Pazianos, G.; Zhao, C.; Yoon, K.; Cook, J.M.; Willert, K.; Gaiano, N. & Reya, T. Integration of Notch and Wnt signaling in hematopoietic stem cell maintenance. Nat Immunol 6, 314-322, doi:ni1164 [pii]10.1038/ni1164 (2005).
Ebert, A. D., Liang, P. & Wu, J. C. Induced Pluripotent Stem Cells as a Disease Modeling and Drug Screening Platform. J Cardiovasc Pharm 60, 408-416, doi:Doi 10.1097/Fjc.0b013e318247f642 (2012).
Garaycoechea, J. I.; Crossan, G.P.; Langevin, F.; Daly, M.; Arends, M.J. & Patel, K.J. Genotoxic consequences of endogenous aldehydes on mouse haematopoietic stem cell function. Nature 489, 571-575, doi:10.1038/nature11368nature11368 [pii] (2012).
Gerber, J. M.; Smith, B.D.; Ngwang, B.; Zhang, H.; Vala, M.S.; Morsberger, L; Galkin, S.; Collector, M.I.; Perkins, B.; Levis, M.J.; Griffin, C.A.; Sharkis, S.J.; Borowitz, M.J.; Karp, J.E. & Jones, R.J. A clinically relevant population of leukemic CD34(+)CD38(-) cells in acute myeloid leukemia. Blood 119, 3571-3577, doi:blood-2011-06-364182 [pii] 10.1182/blood-2011-06-364182 (2012).

(Continued)

*Primary Examiner* — Emily A Cordas
(74) *Attorney, Agent, or Firm* — Casimir Jones, S.C.; Jeffrey W. Childers

(57) ABSTRACT

A detectable substrate for aldehyde dehydrogenase (ALDH) can be used for selecting cells that express ALDH. The detectable substrate can have a fluorescent moiety that has an excitation wavelength, an emission wavelength, or both, that does not overlap with the excitation wavelength, emission wavelength, or both, of green fluorescent protein.

9 Claims, 18 Drawing Sheets

(56) References Cited

OTHER PUBLICATIONS

Hassner, A., Birnbaum, D. & Loew, L. M. Charge-Shift Probes of Membrane-Potential-Synthesis. J Org Chem 49, 2546-2551, doi:Doi 10.1021/Jo00188a006 (1984).
Hess, D. A.; Meyerrose, T.E.; Wirthlin, L.; Craft, T.P.; Herrbrich, P.E.; Creer, M.H. & Nolta, J.A. Functional characterization of highly purified human hematopoietic repopulating cells isolated according to aldehyde dehydrogenase activity. Blood 104, 1648-1655, doi:DOI 10.1182/blood-2004-02-0448 (2004).
Hilton, J. Role of aldehyde dehydrogenase in cyclophosphamide-resistant L1210 leukemia. Cancer Res 44, 5156-5160 (1984).
Inoue, H. & Yamanaka, S. The Use of Induced Pluripotent Stem Cells in Drug Development. Clin Pharmacol Ther 89, 655-661, doi:Doi 10.1038/Clpt.2011.38 (2011).
Jones, R. J.; Barber, J.P.; Vala, M.S.; Collector, M.I.; Kaufmann, S.H.; Ludeman, S.M.; Colvin, O.M. & Hilton, J. Assessment of aldehyde dehydrogenase in viable cells. Blood 85, 2742-2746 (1995).
Levi, B. P., Yilmaz, O. H., Duester, G. & Morrison, S. J. Aldehyde dehydrogenase 1a1 is dispensable for stem cell function in the mouse hematopoietic and nervous systems. Blood 113, 1670-1680, doi:blood-2008-05-156752 [pii] 10.1182/blood-2008-05-156752 (2009).
Ma, I. & Allan, A. L. The role of human aldehyde dehydrogenase in normal and cancer stem cells. Stem Cell Rev 7, 292-306, doi:10.1007/s12015-010-9208-4 (2011).
Marchitti, S. A., Brocker, C., Stagos, D. & Vasiliou, V. Non-P450 aldehyde oxidizing enzymes: the aldehyde dehydrogenase superfamily. Expert Opin Drug Metab Toxicol 4, 697-720, doi:10.1517/17425255.4.6.697 (2008).
Niederreither, K., Subbarayan, V., Dolle, P. & Chambon, P. Embryonic retinoic acid synthesis is essential for early mouse post-implantation development. Nat Genet 21, 444-448, doi:10.1038/7788 (1999).
Pajcini, K. V., Speck, N. A. & Pear, W. S. Notch signaling in mammalian hematopoietic stem cells. Leukemia 25, 1525-1532, doi:10.1038/leu.2011.127leu2011127 [pii] (2011).
Pearce, D. J. & Bonnet, D. The combined use of Hoechst efflux ability and aldehyde dehydrogenase activity to identify murine and human hematopoietic stem cells. Exp Hematol 35, 1437-1446, doi:S0301-472X(07)00353-0 [pii]10.1016/j.exphem.2007.06.002 (2007).
Rovira, M.; Scott, S.G.; Liss, A.S.; Jensen, J.; Thayer, S.P. & Leach, S.D. Isolation and characterization of centroacinar/terminal ductal progenitor cells in adult mouse pancreas. Proc Natl Acad Sci U S A 107, 75-80, doi:0912589107 [pii]10.1073/pnas.0912589107 (2010).
Shapiro, H. M. Practical flow cytometry. 4th edn, (Wiley-Liss, 2003).
Shima, K.; Mizuma, M.; Hayashi, H.; Nakagawa, K.; Okada, T.; Sakata, N.; Omura, N.; Kitamura, Y.; Motoi, F.; Rikiyama, T.; Katayose, Y.; Egawa, S.; Ishii, N.; Horii, A. & Unno, M. Potential utility of eGFP-expressing NOG mice (NOG-EGFP) as a high purity cancer sampling system. J Exp Clin Cancer Res 31, 55, doi:1756-9966-31-55 [pii] 10.1186/1756-9966-31-55 (2012).
Sison-Young, R. L. C.; Kia R.; Heslop, J.; Kelly, L.; Rowe, C.; Cross, M.J.; Kitteringham, N.R.; Hanley, N.; Park, B.K. & Goldring, C.E. Human Pluripotent Stem Cells for Modeling Toxicity. Adv Pharmacol 63, 207-256, doi:Doi 10.1016/B978-0-12-398339-8.00006-9 (2012).
Stevens, A.C.; Frutos, R.P.; Harvey, D.F.; Brian, A.A. Synthesis of protein-reactive (aminostyryl)pyridinium dyes. Bioconj. Chem. 4:19-24 (1993).
Storms, R.W., Trujillo, A.P.: Springer, J.B.: Shah, L.: Colvin, O.M.: Ludeman, S.M.: Smith, C. Isolation of primitive human hematopoietic progenitors on the basis of aldehyde dehydrogenase activity. Proc Natl Acad Sci USA 96, 9118-9123 (1999).
Tiscornia, G., Vivas, E. L. & Belmonte, J. C. I. Diseases in a dish: modeling human genetic disorders using induced pluripotent cells. Nat Med 17, 1570-1576, doi:Doi 10.1038/Nm.2504 (2011).
Vaidyanathan, G.; Song, H., Affleck, D., McDougald, D.L., Storms, R.W.; Zalutsky, M.R. & Chin, B.B. Targeting aldehyde dehydrogenase: a potential approach for cell labeling. Nucl Med Biol 36, 919-929, doi:DOI 10.1016/j.nucmedbio.2009.08.001 (2009).
Vasiliou, V., Pappa, A. & Estey, T. Role of human aldehyde dehydrogenases in endobiotic and xenobiotic metabolism. Drug Metab Rev 36, 279-299, doi:10.1081/DMR-120034001 (2004).
Wuskell, J.P.; Boudreau, D.; Wei, M.D.; Jin, L.; Engl, R.; Chebolu, R.; Bullen, A.; Hoffacker, K.D.; Kerimo, J.; Cohen, L.B.; Zochowski, M.R.; Loew, L.M. Synthesis, spectra, delivery and potentiometric responses of new styryl dyes with extended spectral ranges. J. Neuroscience Methods 151: 200-215 (2006).
7hang Y.; Byun, Y.; Ren, Y.R.; Liu, J.O.; Laterra, J.; Pomper, M.G. Identification of inhibitors of ABCG2 by a bioluminescence imaging-based high-throughput assay. Cancer Res. 69(14), 5867-5875 (2009).
Storms, R et al. Isolation of Primitive Human Hematopoietic Progenitors on the Basis of Aldehyde Dehydrogenase Activity. PNAS. Aug. 3, 1999, vol. 96; pp. 9118-9123.
International Search Report and Written Opinion dated May 14, 2014 from PCT International Application No. PCT/US2014/017735.
"Technical Bulletin: Identification of viable stem and progenitor cells with Aldefluor(R)", Jul. 2009, pp. 1-4.
Extended European Search Report dated Jun. 24, 2016 for a corresponding European patent application No. 14753892.0.

\* cited by examiner

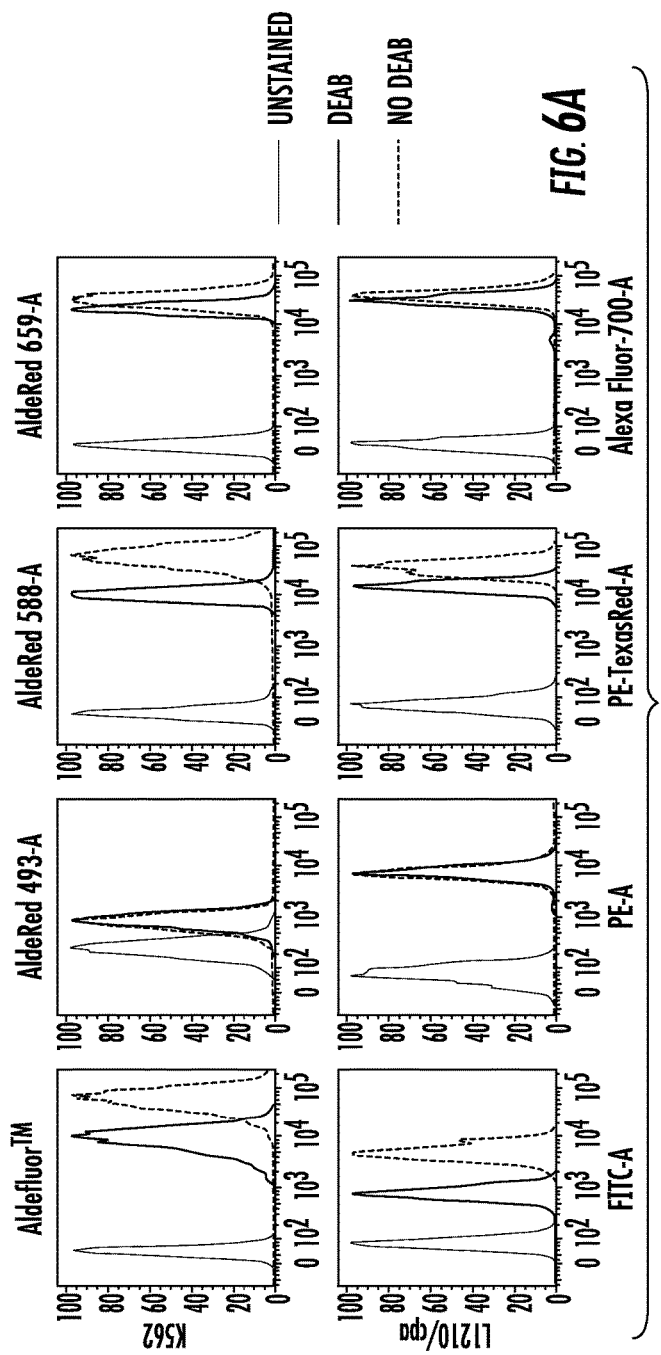
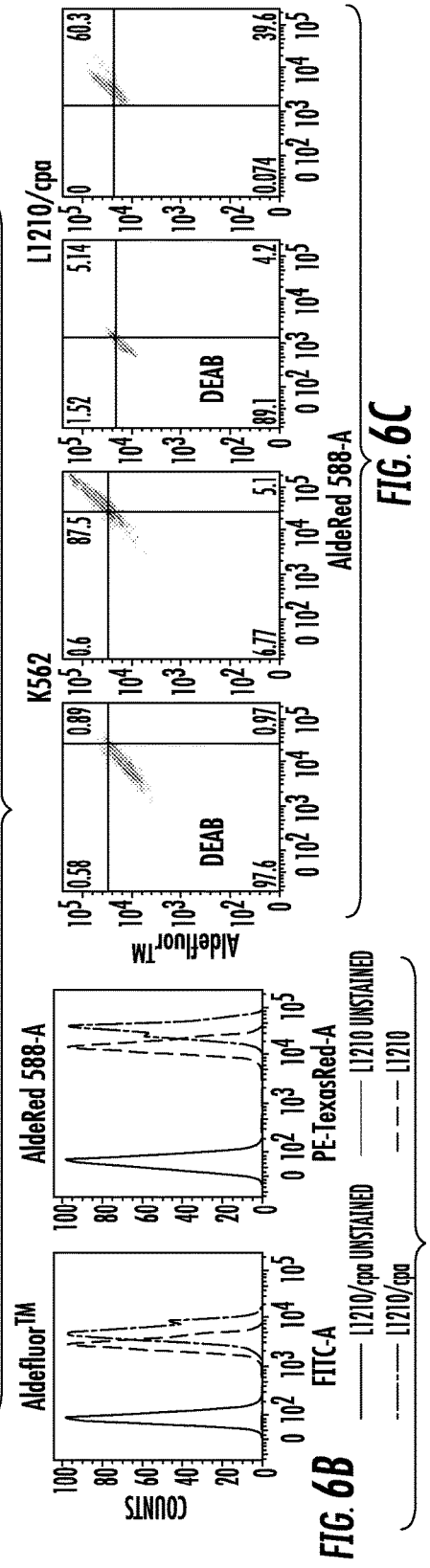
FIG. 6A
FIG. 6B
FIG. 6C

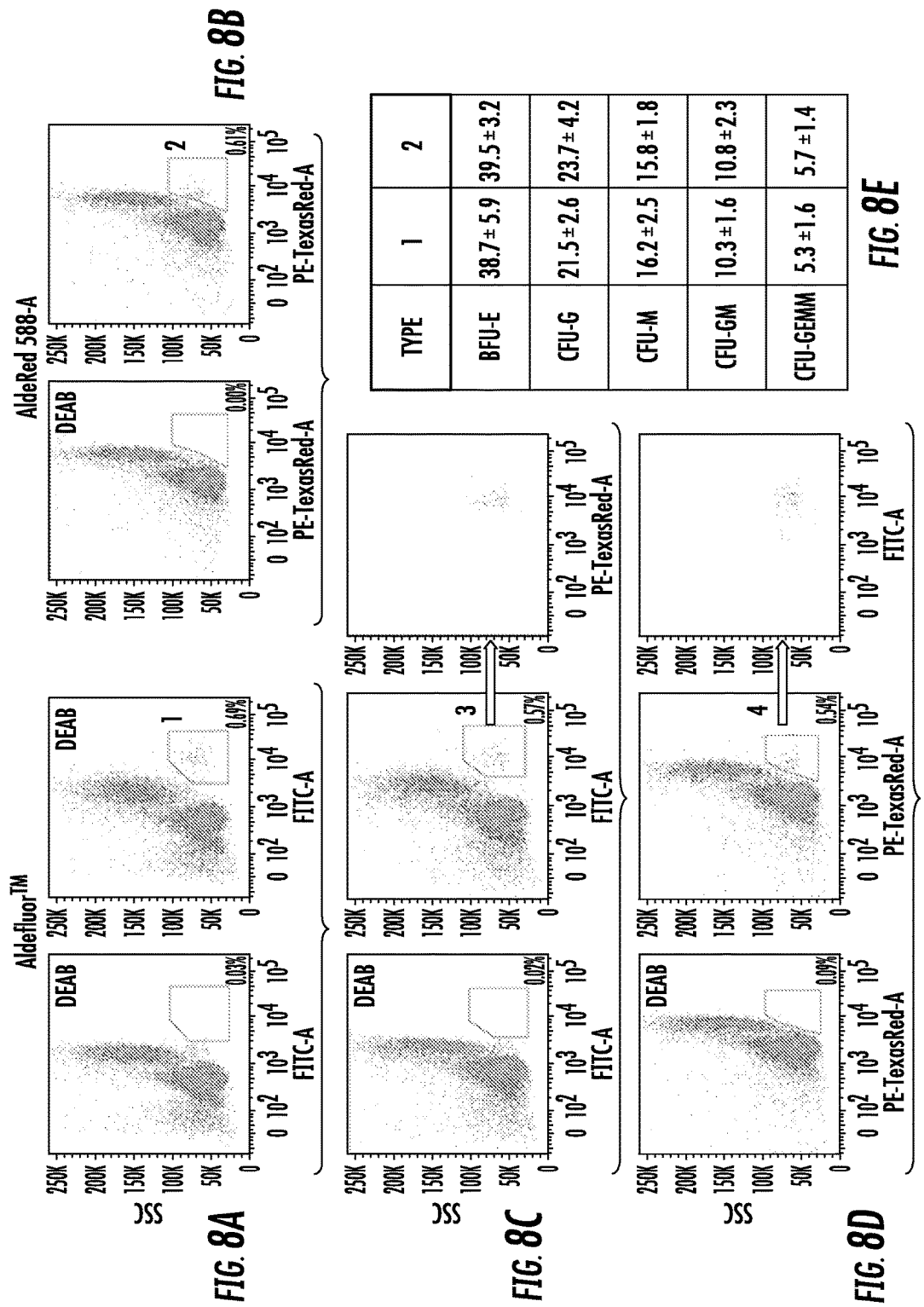

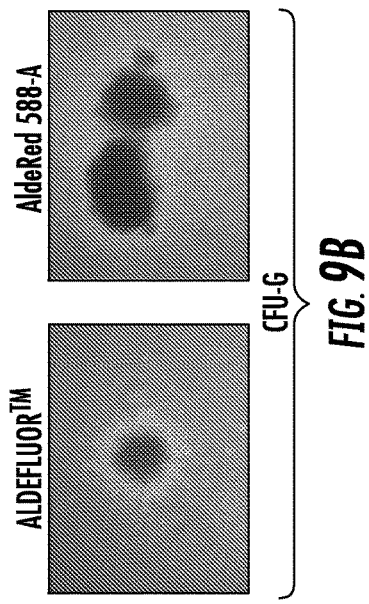
FIG. 9B CFU-G
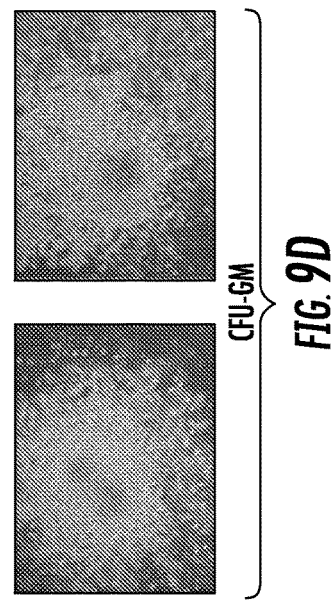
FIG. 9D CFU-GM
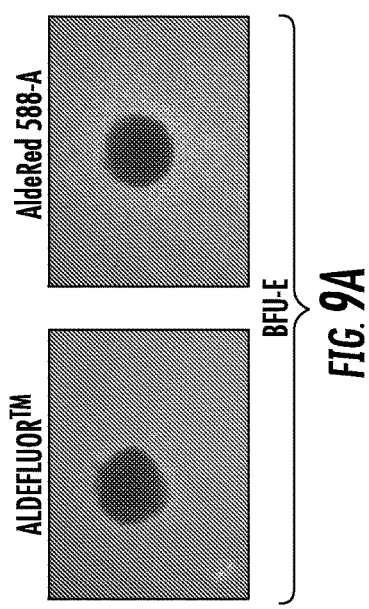
FIG. 9A BFU-E
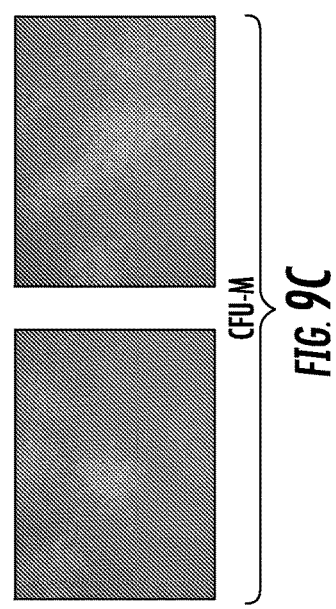
FIG. 9C CFU-M
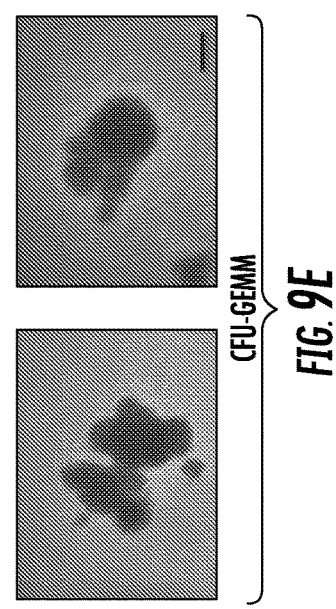
FIG. 9E CFU-GEMM

RED FLUORESCENT ALDEHYDE DEHYDROGENASE (ALDH) SUBSTRATE

CROSS REFERENCE TO RELATED APPLICATIONS

This application is a 35 U.S.C. § 371 National Stage Entry of International Application No. PCT/US2014/017735 having an international filing date of Feb. 21, 2014, which claims the benefit of U.S. Provisional Patent Application No. 61/767,576, filed Feb. 21, 2013, and U.S. Provisional Patent Application No. 61/921,913, filed Dec. 30, 2013, the content of each of which is herein incorporated by reference in their entireties.

FEDERALLY SPONSORED RESEARCH OR DEVELOPMENT

This invention was made with government support under grant no. DK056211 awarded by the National Institutes of Health. The government has certain rights in the invention.

BACKGROUND

Aldehyde dehydrogenase (ALDH) is an evolutionarily conserved enzyme with pyridine nucleotide dependent oxidoreductase activity that performs a variety of critical cellular processes (Marchitti et al., 2008). These processes include production of retinoic acid essential for mammalian development (Niederreither et al., 1999), metabolism of fats and amino acids, and detoxification of endogenous and exogenous sources of hazardous aldehyde byproducts (Vasiliou et al., 2004). Twenty human ALDH genes have been identified, but many of their functions are still unknown (Black et al., 2009).

Stem cells are important new reagents in biomedical research. They can provide experimental models for target discovery (Tiscornia et al., 2011) or toxicity testing (Sison-Young et al., 2012) and can be used as tools for screening drugs and in developing therapies for a host of disorders (Ebert et al., 2012; Inoue and Yamanaka, 2011). Stem cells also can provide a direct source of materials for regenerative medicine (Cherry and Daley, 2013). The ability to prepare pure, undamaged and functionally active stem cells is the critical first step for all such applications.

Isolation of stem cells is generally accomplished by selection with monoclonal antibodies that recognize stem cell-specific cell surface markers or by utilizing functional markers of stem cell activity, such as elevated expression of multi-drug efflux pumps (Bunting, 2002) and ALDH (Jones et al., 1995). Combinations of multiple markers, which often require multiple steps of selection, are used to isolate rare stem cells from heterogeneous cell populations. A brief, single-step isolation method would be preferred to minimize loss of and damage to rare stem cells.

For the past two decades, ALDH has been studied as a potential universal marker for normal and cancer stem cells as certain isoenzymes of the ALDH superfamily have been identified as key elements of these cells (Ma and Allan, 2011). For example, Aldh1a1 and Aldh3a1 have been implicated in the protection of stem cells from cytotoxic drugs. $ALDH^{pos}$ stem cells have been used as resources for regenerative medicine in preclinical models (Balber, 2011) and in an ongoing clinical trial for ischemic cardiomyopathy (clinicaltrial.gov, NCT00314366). ALDH1 has been identified as a marker used to isolate cancer stem cells of various human malignancies including bladder, breast, cervical, colon, head and neck, liver, lung, pancreas, prostate, and ovary (Ma and Allan, 2011). Recently Gerber et al. showed that the presence of leukemic stem cells with intermediate ALDH activity ($ALDH^{int}$) could be used as a predictor for relapse after therapy, whereas normal hematopoietic stem cells (HSCs) retain high ALDH activity (Gerber et al., 2012). Since these normal and cancer stem cells are very rare, methods to identify and isolate viable, functionally active $ALDH^{pos}$ cells are needed to characterize or utilize them.

The ALDEFLUOR™ reagent (Aldagen Inc., Durham, N.C.) has enabled the primary commercial assay used today for isolation of viable $ALDH^{pos}$ cells, which was patterned after the original dansyl aminoacetaldehyde (DAAA) based assay developed by Jones et al. (1995). Although very sensitive and specific for staining viable $ALDH^{Pos}$ cells, because it emits in the green region of the electromagnetic spectrum (512 nm), the ALDEFLUOR™ reagent cannot be simultaneously utilized in cells or mice expressing green fluorescent proteins (Shima et al., 2012; Duncan et al., 2005). This characteristic has limited the use of many valuable cell and animal models with green fluorescent signals to study ALDH.

SUMMARY

In one aspect, the presently disclosed subject matter provides a detectable substrate for ALDH of formula (I):

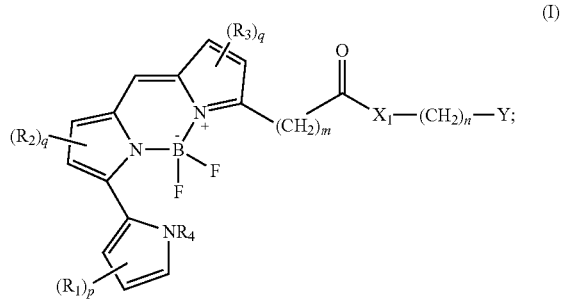

wherein: m and n are each independently an integer selected from the group consisting of 1, 2, 3, 4, 5, 6, 7, and 8; p is an integer selected from the group consisting of 0, 1, 2, and 3; each q is independently an integer selected from the group consisting of 0, 1, and 2; each $R_1$, $R_2$, and $R_3$ is independently selected from the group consisting of H, halogen, —OH, nitro, cyano, —O-alkyl, alkyl, alkenyl, alkynyl, cycloalkyl, heterocycloalkyl, cycloalkenyl, heterocycloalkenyl, aryl, or heteroaryl, optionally substituted by one to five substituents selected from H, halogen, alkyl, alkenyl, alkynyl, cycloalkyl, cycloalkenyl, heterocycloalkyl, heterocycloalkenyl, —OH, —O-alkyl, nitro, cyano, aryl, or heteroaryl; $R_4$ is selected from the group consisting of H, alkyl, alkoxyl, cycloalkyl, cycloheteroalkyl, aryl, and heteroaryl; $X_1$ is selected from the group consisting of $NR_5$, O, and S, wherein $R_5$ is selected from the group consisting of H, alkyl, alkoxyl, and aryl; Y is selected from the group consisting of —CH(=O); C(=O)—O⁻; and —CH(OCH₂CH₃)₂; and wherein the compound of formula (I) has a peak emission wavelength of 530 nm or greater.

In particular aspects, the detectable ALDH substrate can have a peak emission wavelength that is longer than the peak emission wavelength of a fluorescent protein, if present in the mixed population of cells by about 30 nm or more. In some aspects, the mixed population of cells can be contacted with the detectable ALDH substrate in the presence of a multi-drug efflux pump inhibitor having inhibitory action against ABCB1, ABCG2, or having dual inhibitory action against both ABCB1 and ABCG2.

In yet other aspects, the presently disclosed methods can further include isolating the identified cells exhibiting an increased fluorescence. The isolated cells can include stem cells.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1A:
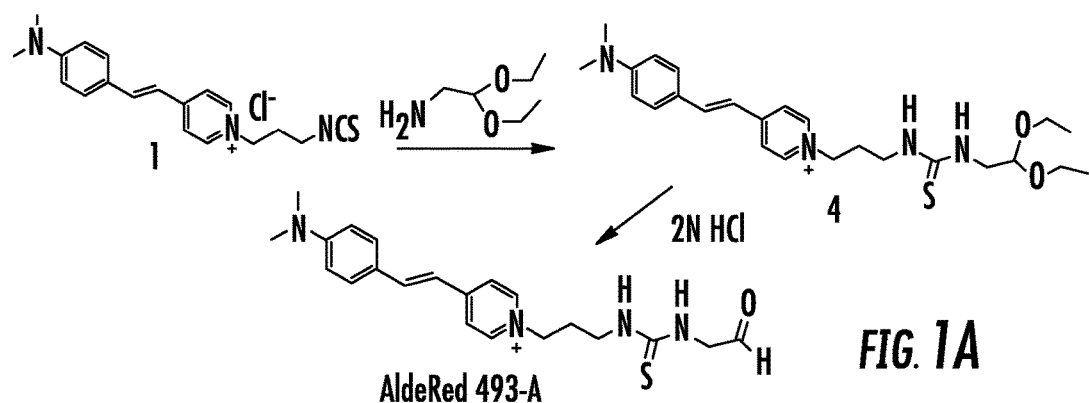
Figure 1B:
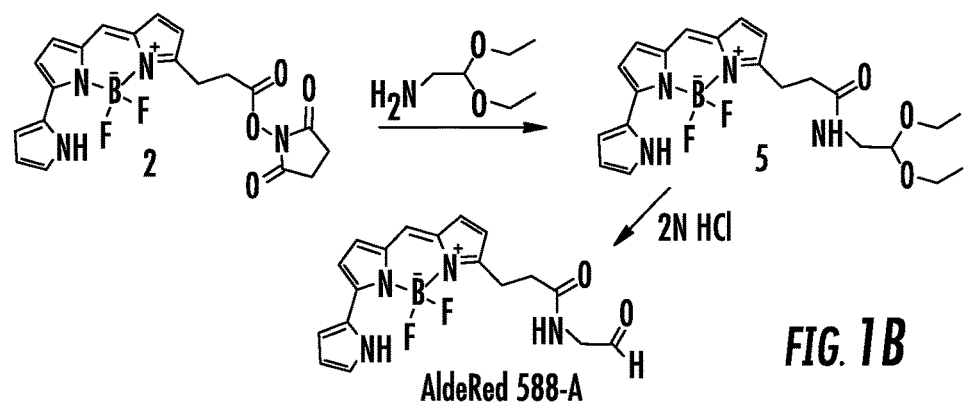
Figure 1C:
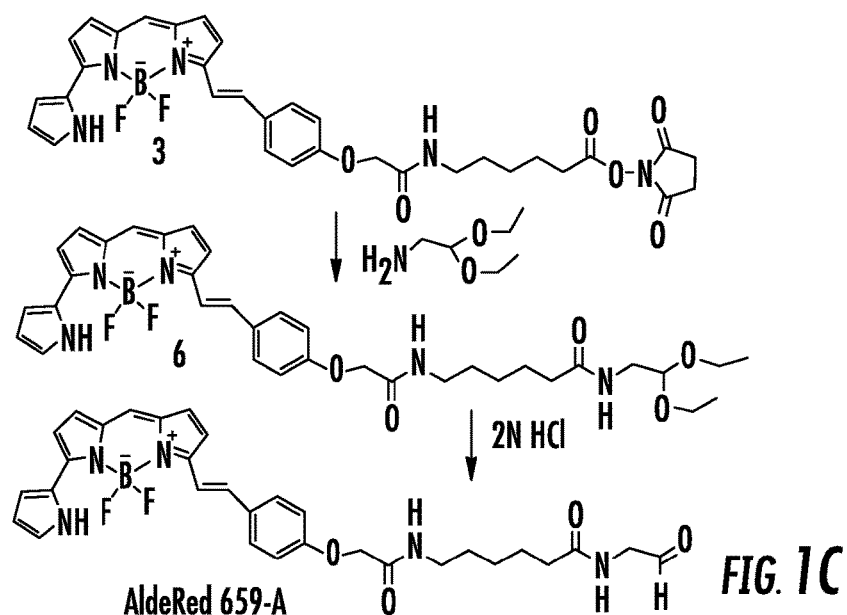
Figure 2A:
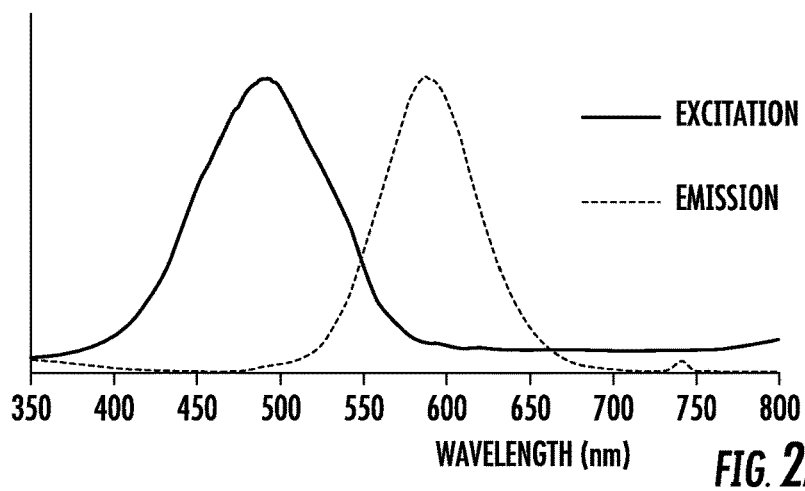
Figure 2B:
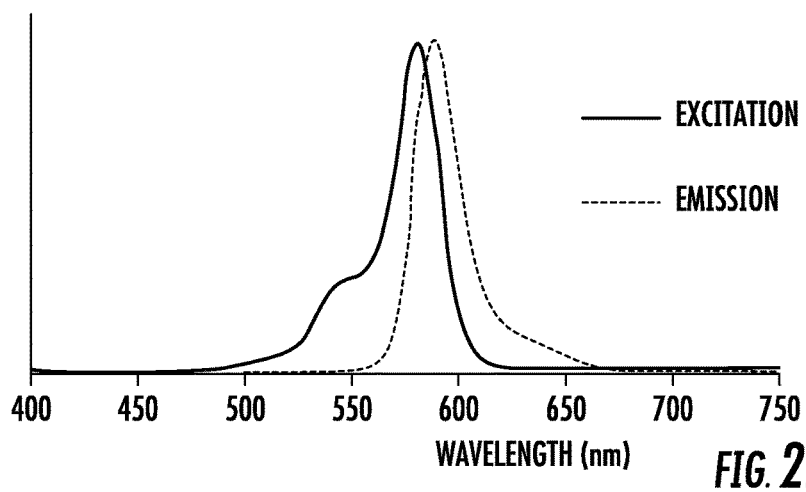
Figure 2C:
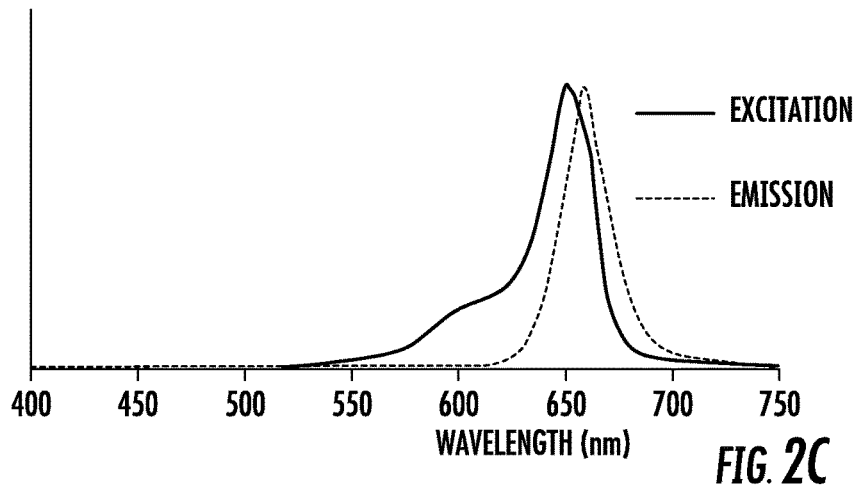
Figure 3:
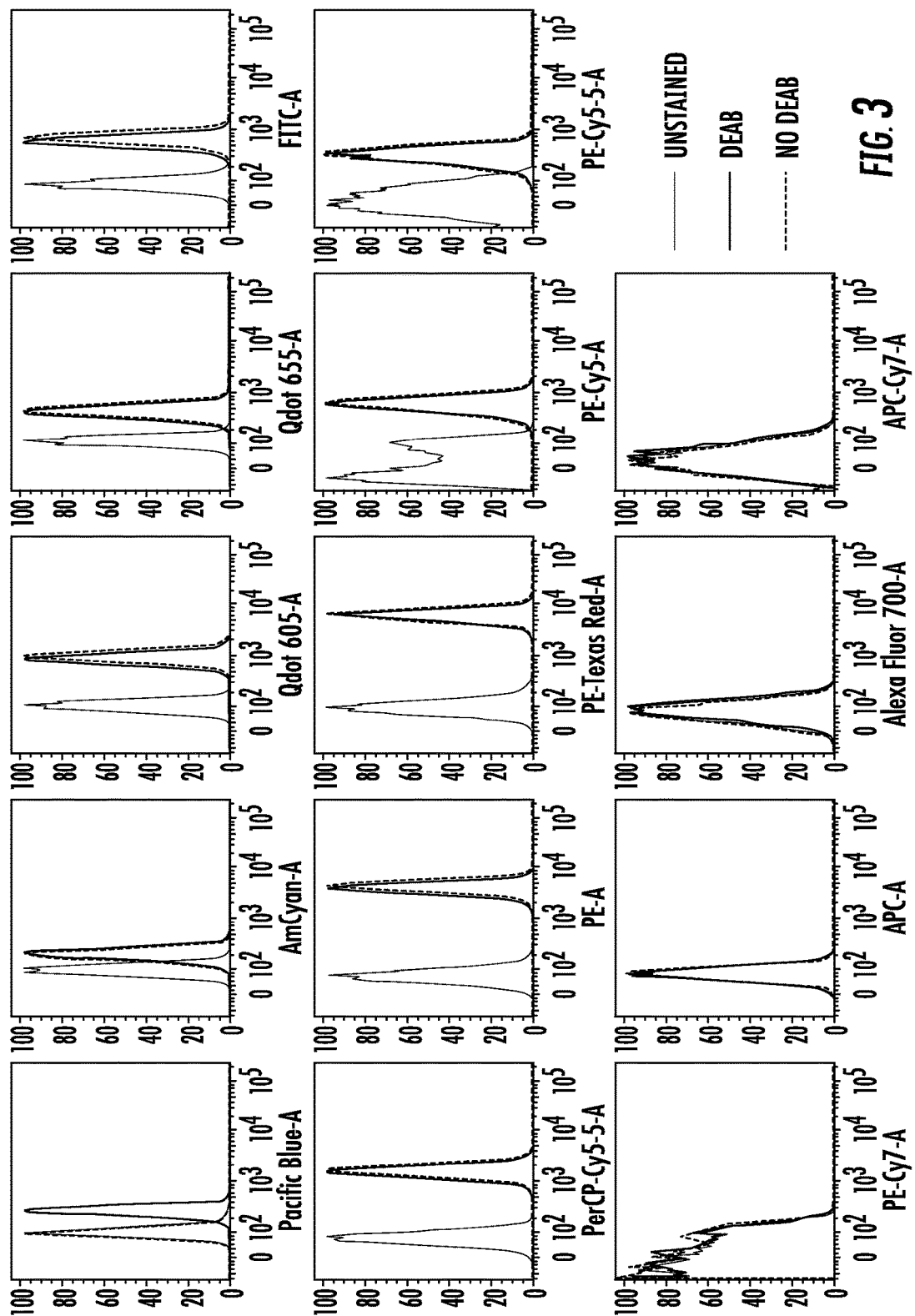
Figure 4:
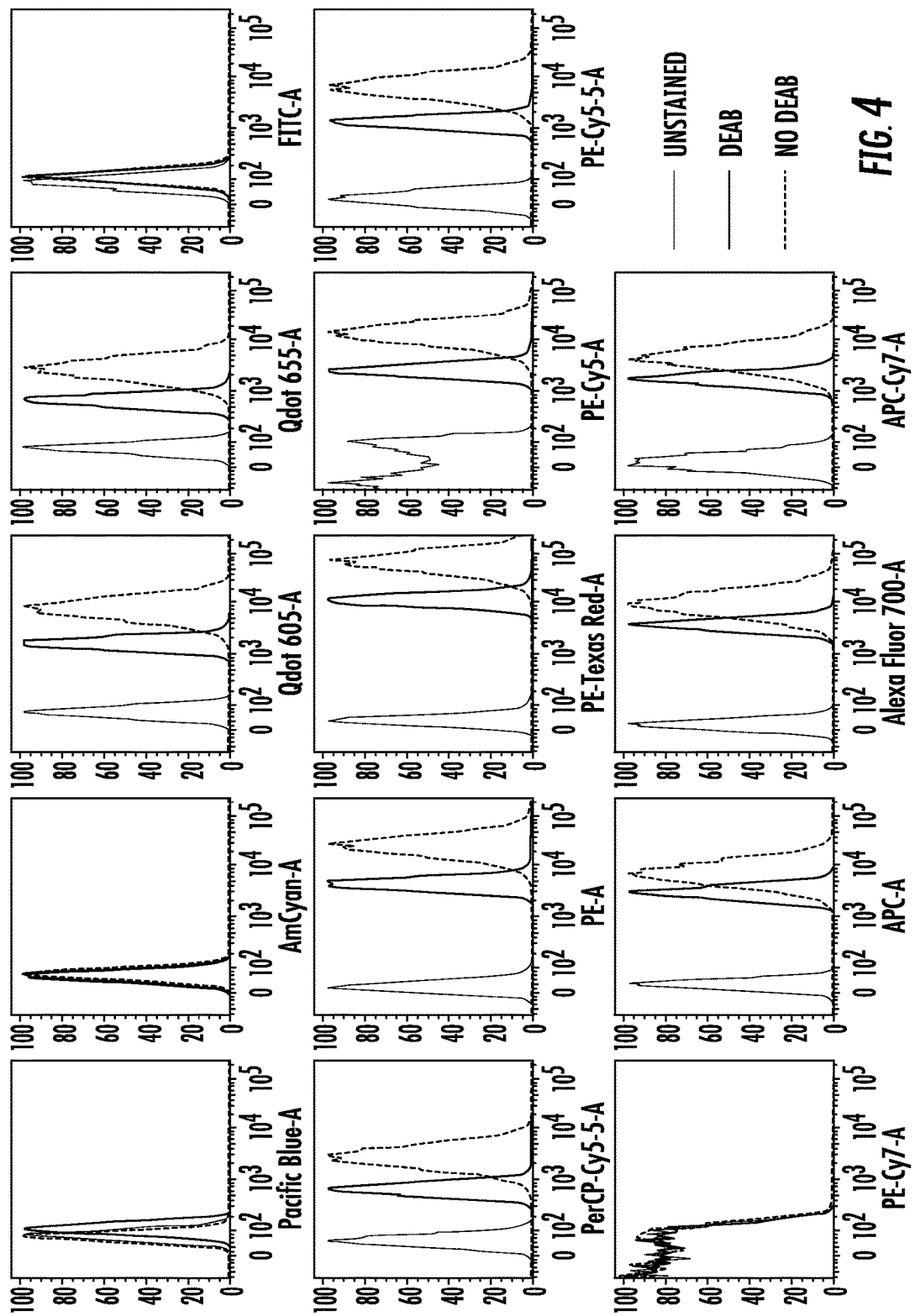
Figure 5:
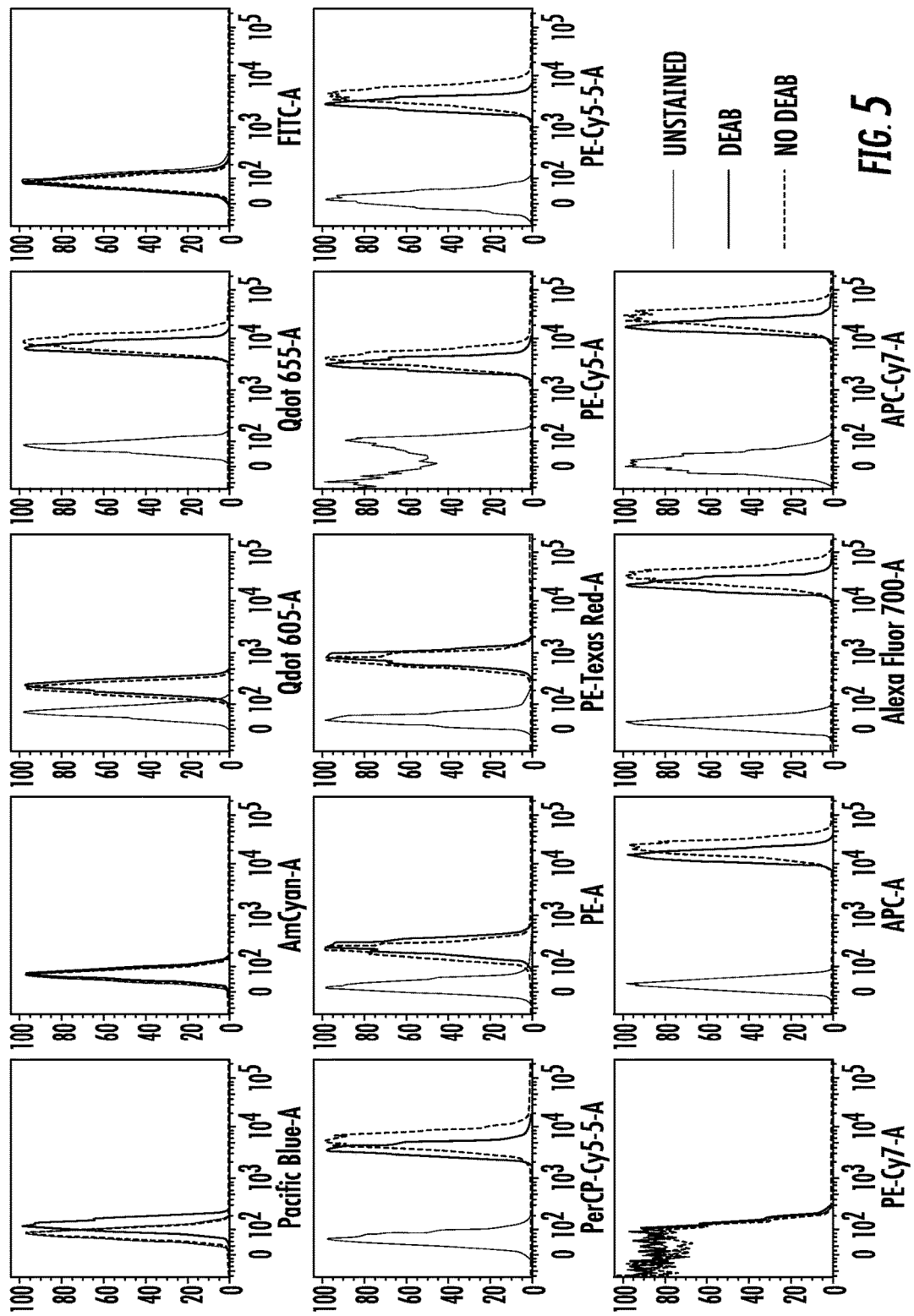
Figure 7:
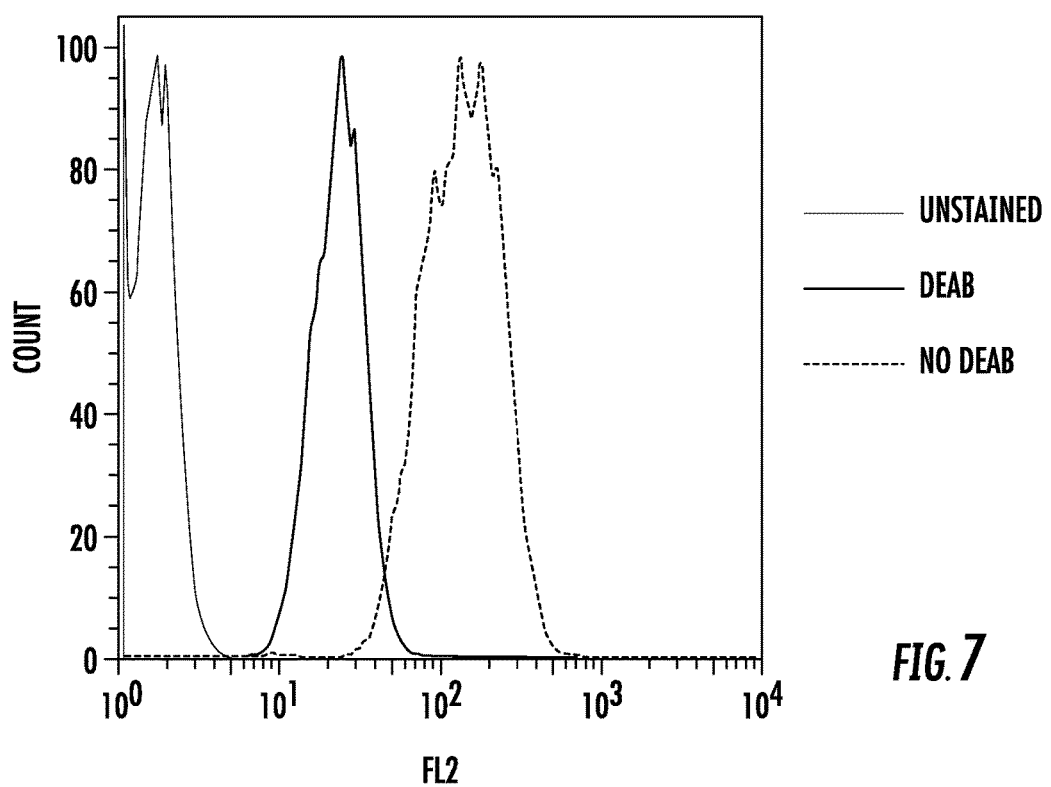
Figure 10:
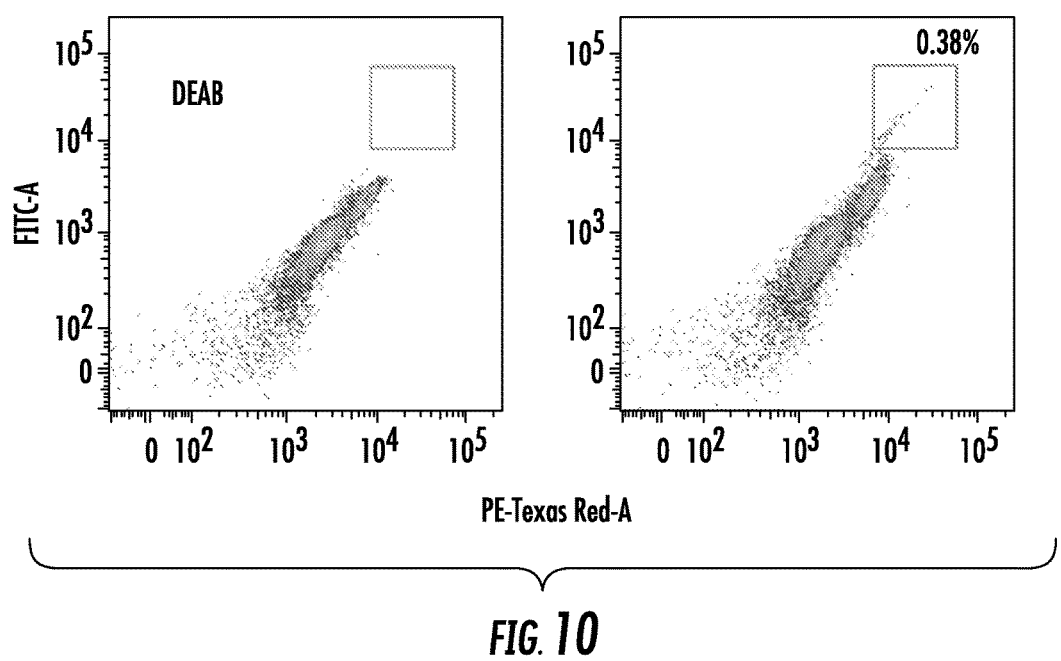
Figure 12A:
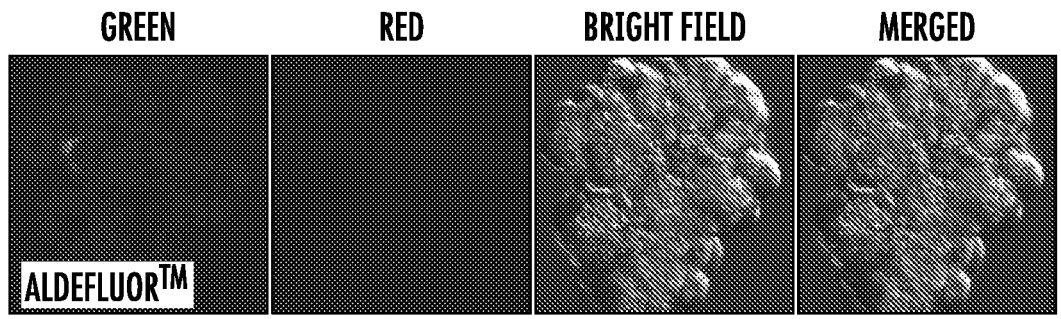
Figure 12B:
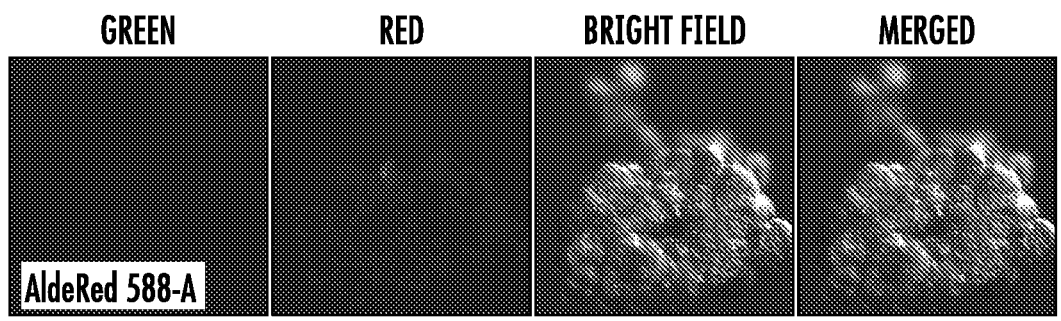
Figure 12C:
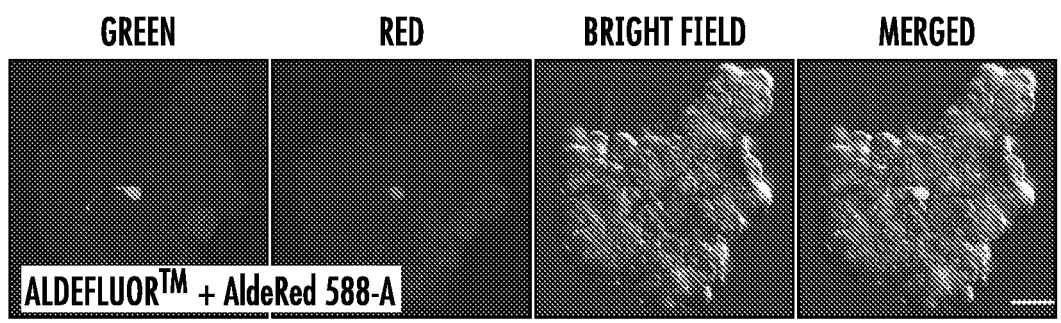
Figure 13:
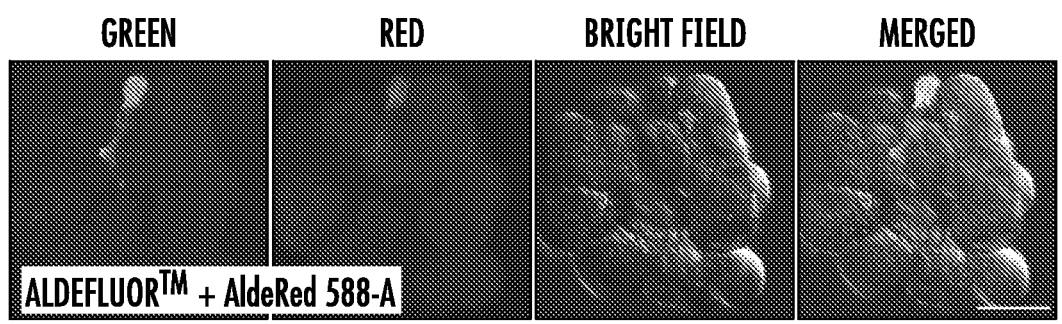
Figure 14A:
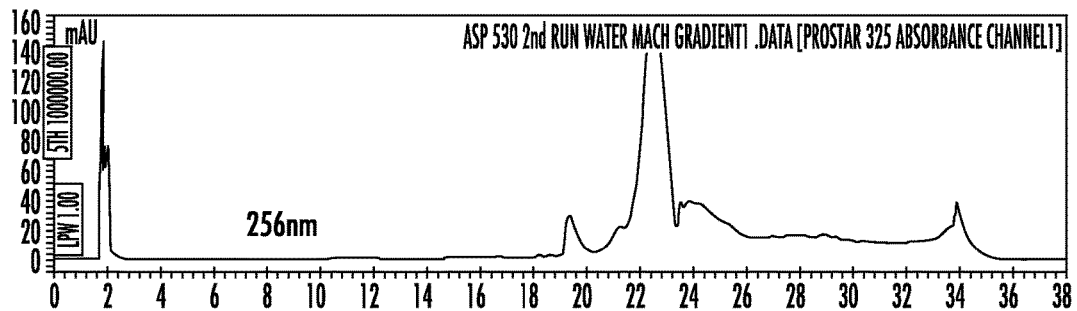
Figure 14B:
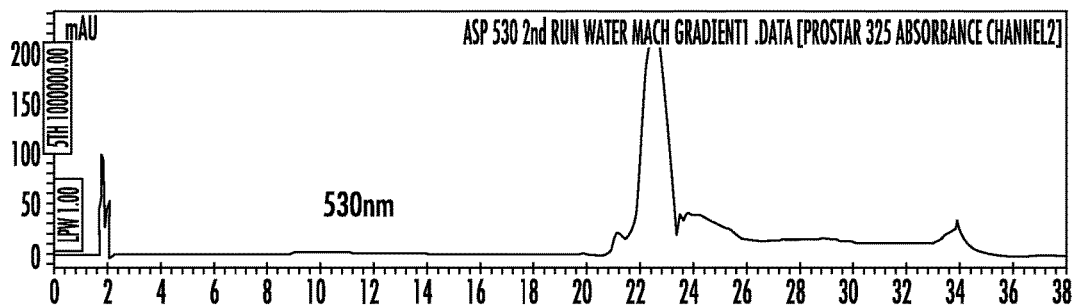
Figure 14C:
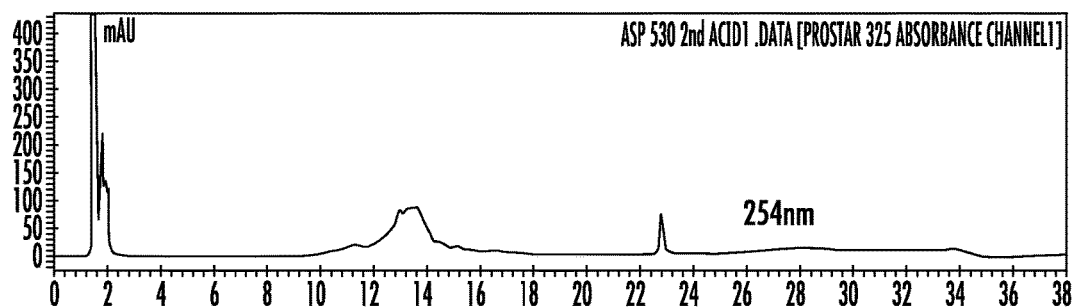
Figure 14D:
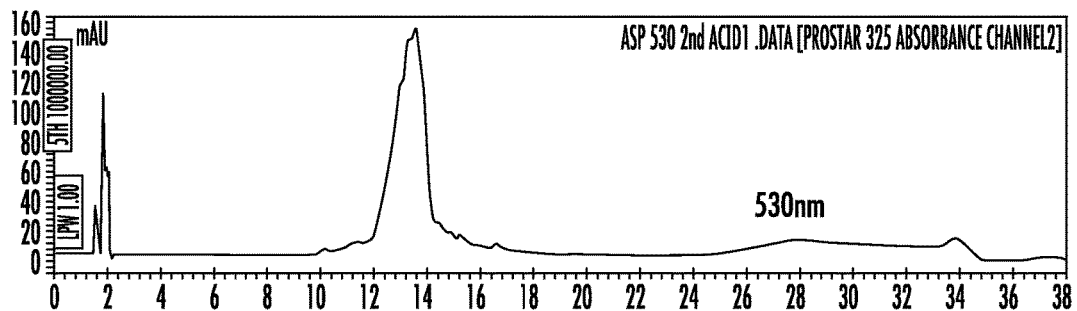
Figure 15A:
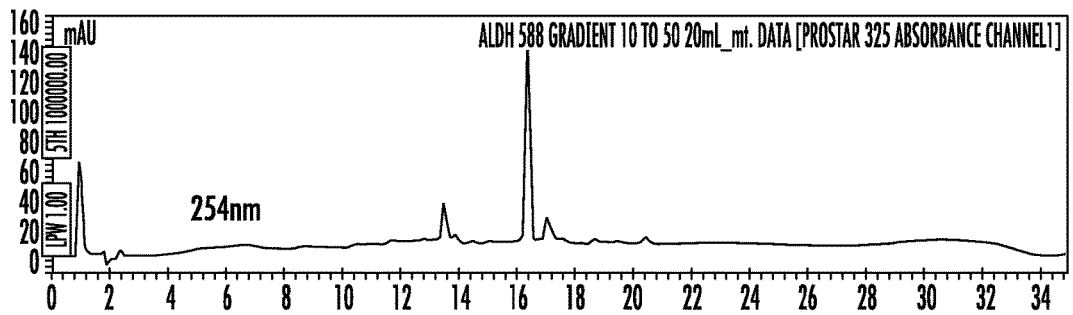
Figure 15B:
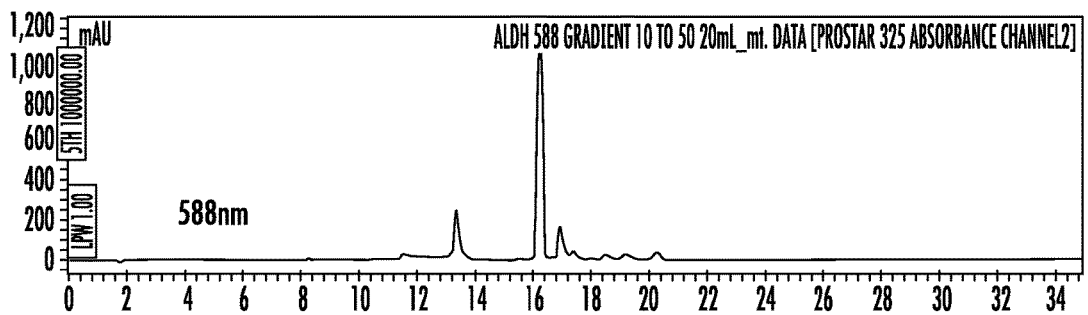
Figure 15C:
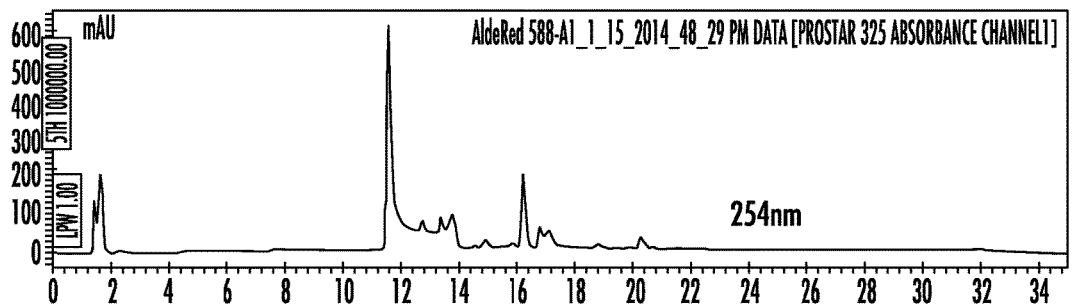
Figure 15D:
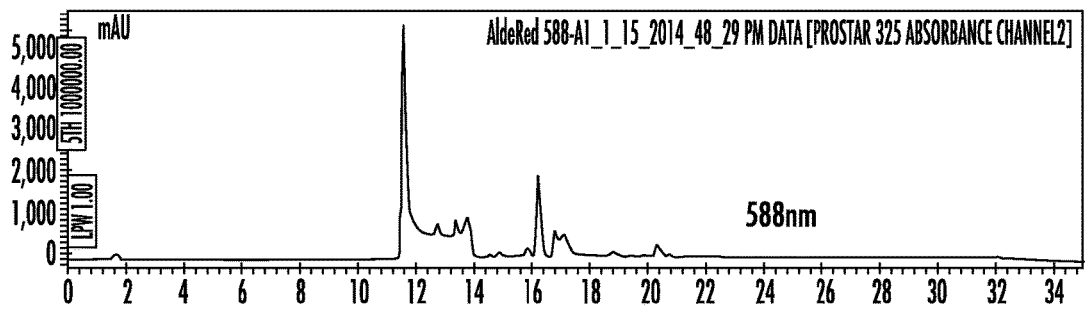
Figure 16A:
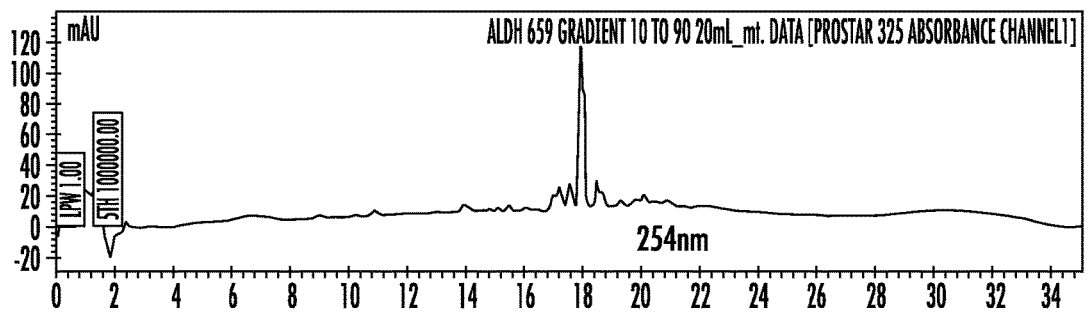
Figure 16B:
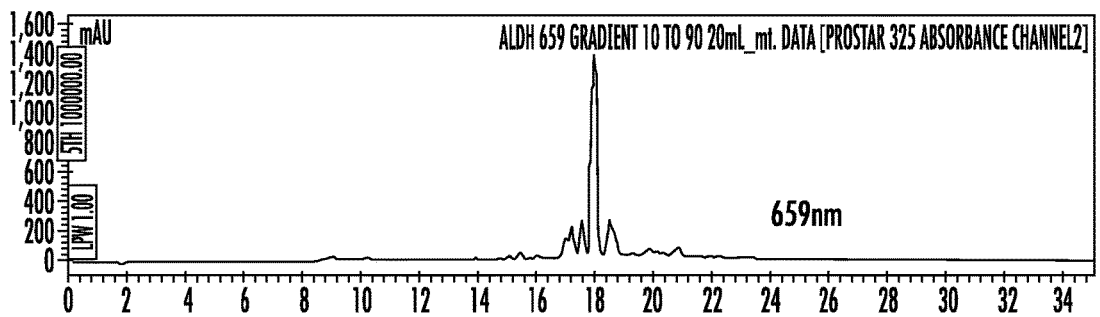
Figure 16C:
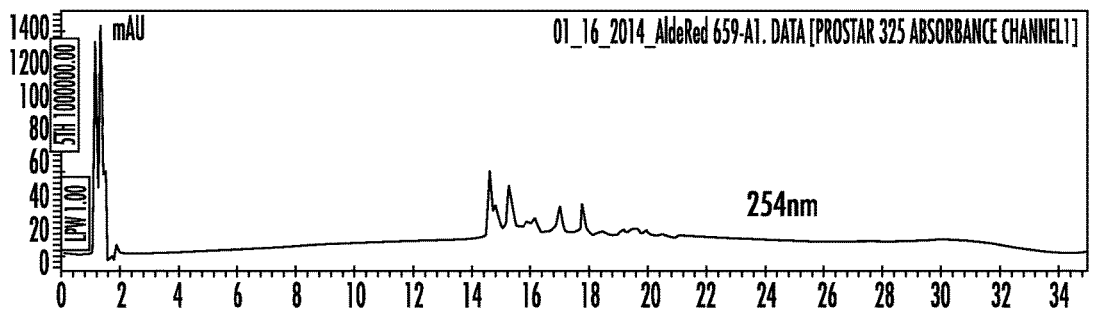
Figure 16D:
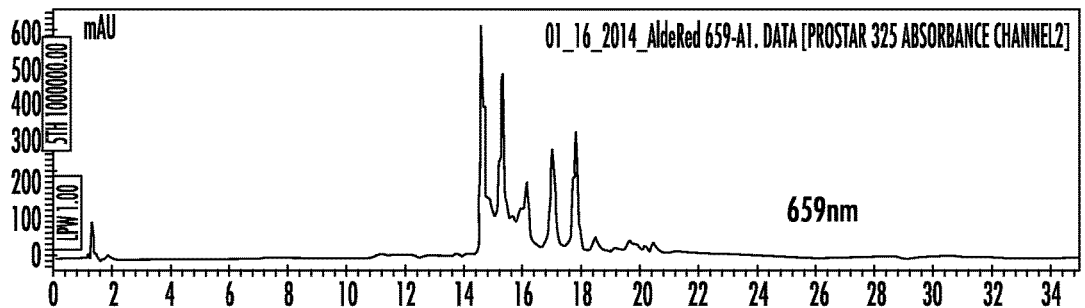
Figure 17A:
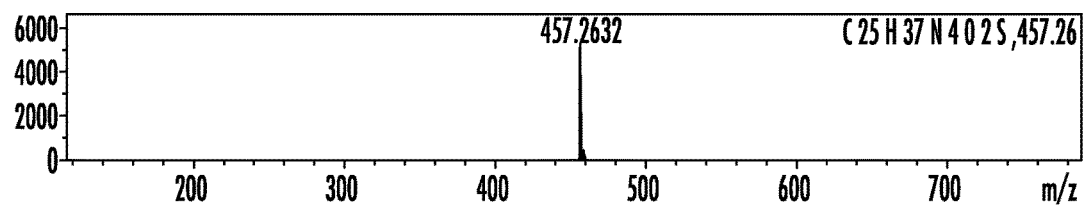
Figure 17B:
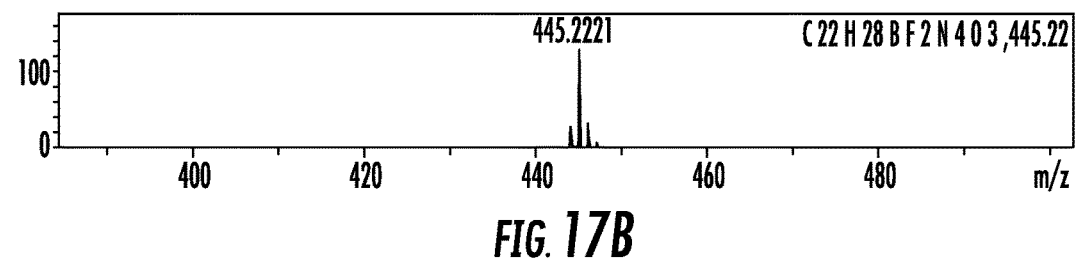
Figure 17C:
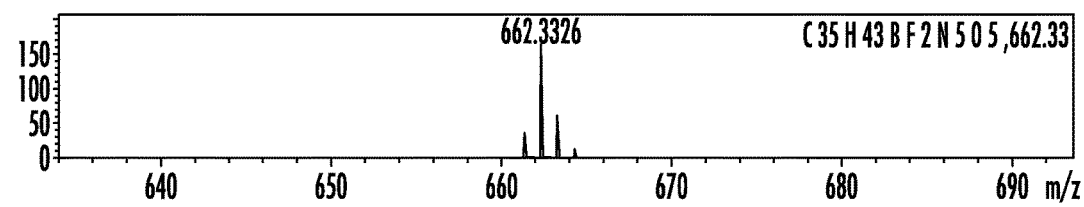
Figure 18:
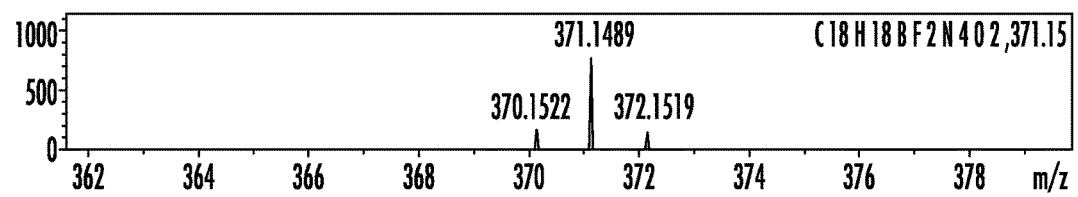

Having thus described the presently disclosed subject matter in general terms, reference will now be made to the accompanying Figures, which are not necessarily drawn to scale, and wherein:

FIGS. 1a-1c show the synthesis and in vitro validation of representative red-shifted fluorescent substrates for aldehyde dehydrogenase (ALDH): (a) AldeRed 493-A; (b) AldeRed 588-A; and (c) AldeRed 659-A. Each compound was prepared as the diacetal (4, 5, and 6) and deprotected to the aldehyde prior to use;

FIGS. 2a-2c show the excitation and emission profiles of candidate ALDH substrates. (a) AldeRed 493 aldehyde diethyl acetal, (b) AldeRed 588 aldehyde diethyl acetal, (c) AldeRed 659 aldehyde diethyl acetal. All the compounds were dissolved in 100% ethanol and both excitation and emission profiles were measured in 100% ethanol. The emission spectrum was measured with excitation at 493 nm for AldeRed 493 aldehyde diethyl acetal, at 560 nm for AldeRed 588, and at 650 nm for AldeRed 659-A. Blue line: excitation spectrum; red line: emission spectrum;

FIG. 3 shows fluorescence activated cell sorting (FACS) analyses of AldeRed 493-A with four lasers and 14 emission filters. The human chronic myeloid leukemia cell line K562 (ALDH$^{hi}$) was stained with AldeRed 493-A and analyzed using the LSR II flow cytometer (BD Biosciences, San Jose, CA) equipped with four lasers (405 nm, 488 nm, 532 nm and 633 nm) and 14 emission filters (x-axis). Gray line: unstained cells; black line: cells treated with DEAB (control); and dashed line: cells stained with AldeRed 493-A;

FIG. 4 shows FACS analyses of AldeRed 588-A with four lasers and 14 emission filters. The human chronic myeloid leukemia cell line K562 (ALDH$^{hi}$) was stained with AldeRed 588-A and analyzed using the LSR II flow cytometer equipped with four lasers (405 nm, 488 nm, 532 nm, and 633 nm) and 14 emission filters (x-axis). Gray line: unstained cells; black line: cells treated with DEAB (control); and dashed line: cells stained with AldeRed 588-A;

FIG. 5 shows fluorescence activated cell sorting (FACS) analyses of AldeRed 659-A with four lasers and 14 emission filters. The human chronic myeloid leukemia cell line K562 (ALDH$^{hi}$) was stained with AldeRed 588-A and analyzed using the LSR II flow cytometer equipped with four lasers (405 nm, 488 nm, 532 nm, and 633 nm) and 14 emission filters (x-axis ). Gray line: unstained cells; black line: cells treated with DEAB (control); and dashed line: cells stained with AldeRed 659-A;

FIGS. 6a-6c show that AldeRed 588-A is a specific substrate for ALDH: (a) fluorescent candidates and the ALDEFLUOR™ reagent were tested with K562 and L1210/cpa cells (x-axis represents selected detection filters of the LSRII FACS system); (b) AldeRed 588-A and the ALDEFLUOR™ reagent tested with L1210/cpa and L1210 cells; and (c) co-staining of AldeRed 588-A and the ALDEFLUOR™ reagent with K562 and L1210/cpa cells (DEAB: diethylaminobenzaldehyde);

FIG. 7 shows that cells stained with AldeRed 588-A can be analyzed using a simple analytical flow cytometer with blue laser. The human chronic myeloid leukemia cell line K562 (ALDH$^{hi}$) was stained with AldeRed 588-A and analyzed using FACSCALIBUR$^{TM}$ (BD Biosciences, San Jose, CA). Cells were excited by a 488-nm blue laser with emission detected using the FL2 channel. Gray line: unstained cells; black line: cells treated with DEAB (control); dashed line: cells stained with AldeRed 588-A;

FIGS. 8a-8e show that AldeRed 588-A successfully enabled isolation of ALDH$^{hi}$ hematopoietic stem cells (HSCs) from human cord blood mononuclear cells: (a) ALDEFLUOR™; (b) AldeRed 588-A; (c and d) double staining with ALDEFLUOR™ and AldeRed 588-A. Red boxes represent gating for sorting ALDH$^{hi}$ cells (1 and 2). Numbers at the bottom represent percentage of gated cells. ALDH$^{hi}$ cells (3 and 4) were present in the other channels; and (e) colony-forming cell assays with isolated ALDH$^{hi}$ cells (1 and 2). Numbers represent colonies formed per 500 ALDH$^{hi}$ cells±standard deviation, n=6;

FIGS. 9a-9e show representative photos of colony-forming cell assays. ALDH$^{hi}$ cells isolated via ALDEFLUOR™ (left panel) and AldeRed 588-A (right panel) were cultured in Methocult® H4435 (STEMCELL Technologies, Inc.). Representative photos for BFU-E (a), CFU-G (b), CFU-M (c), CFU-GM (d), and CFU-GEMM (e) are presented. Size bar: 100 μm;

FIG. 10 shows that co-staining of human mononuclear cell with ALDEFLUOR™ and AldeRed 588-A enables isolation of double positive cells. Human cord blood mononuclear cells was stained with ALDEFLUOR™ and AldeRed 588-A in the presence (left) and absence (right) of DEAB. Double positive cells exhibited proportional staining pattern for both reagents indicating high specificity of ALDH staining;

FIGS. 11a-11e show that AldeRed 588-A can enable fractionation of ALDH$^{pos}$ cells from bone marrow (BM) cells from mice that express eGFP: (a-d) fractionation of BM cells based on eGFP expression and AldeRed 588-A uptake levels (numbers represent percentage of each quadrant fraction); (a) DEAB control; (b) sorting of BM cells into five populations (box) for colony-forming assays of sorted cells. BFU-E: burst forming unit-erythroid; CFU-GEMM: colony forming unit-granulocyte, erythrocyte, monocyte, megakaryocyte; CFU-GM: colony forming unit-granulocyte, monocyte; CFU-M: colony forming unit-megakaryocyte. Numbers represent colonies formed per 20,000 eGFP$^{pos}$/ALDH$^{int}$ cells (4) ± standard deviation, n=6; (c and d) enrichment of lineage$^-$/c-Kit$^+$/Sca1$^+$(LKS) hematopoietic stem/progenitor cells (HSPCs) within BM cells. LKS cell populations [gray dots for untreated (c) and black dots for DEAB-treated cells (d)] were back gated on total BM cells (light gray); and (e) representative photos of colony-forming cell assays. The gating strategy (boxes) for the colony forming assay in (b) is superimposed on LKS and BM cell populations (c). Size bar: 100 μm;

FIGS. 12a-12c show that AldeRed 588-A stains ALDH$^{hi}$ murine pancreatic centroacinar and terminal duct (CA/TD) cells. Confocal microscopic images of murine pancreatic CA/TD cells stained with: (a) the ALDEFLUOR™ reagent; (b) AldeRed 588-A; and (c) co-stained with both reagents. Size bar: 20 μm;

FIG. 13 shows that AldeRed 588-A stains ALDH$^{hi}$ murine pancreatic centroacinar and terminal duct (CA/TD) cells. Additional confocal microscopic images of murine pancreatic CA/TD cells co-stained with the ALDEFLUOR™ reagent and AldeRed 588-A. Size bar: 20 μm;

FIGS. 14a-14d show the HPLC chromatograms of AldeRed 493 aldehyde diethyl acetal and its hydrolyzed product. (a, b) AldeRed 493 aldehyde diethyl acetal, (c, d) hydrolyzed products. (a, c) Chromatograms detected at 254 nm. (b, d) Chromatograms detected at 530 nm;

FIGS. 15a-15d show the HPLC chromatograms of AldeRed 588 aldehyde diethyl acetal and its hydrolyzed product. (a, b) AldeRed 588 aldehyde diethyl acetal, (c, d) hydrolyzed products. (a, c) Chromatograms detected at 254 nm. (b, d) Chromatograms detected at 588 nm;

FIGS. 16a-16d show the HPLC chromatograms of AldeRed 659 aldehyde diethyl acetal and its hydrolyzed product. (a, b) AldeRed 659 aldehyde diethyl acetal, (c, d) hydrolyzed products. (a, c) Chromatograms detected at 254 nm. (b, d) Chromatograms detected at 659 nm;

FIGS. 17a-17c show the high resolution mass spectrometry analyses of three candidate ALDH substrates as diacetals. (a) AldeRed 493 aldehyde diethyl acetal, (b) AldeRed 588 aldehyde diethyl acetal, (c) AldeRed 659 aldehyde diethyl acetal. Numbers represent measured mass of each compound; and FIG. 18 shows the high resolution mass spectrometry analysis of isolated AldeRed 588-A.

DETAILED DESCRIPTION

The presently disclosed subject matter now will be described more fully hereinafter with reference to the accompanying Figures, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. Red Fluorescent Aldehyde Dehydrogenase (Aldh) Substrate

The presently disclosed subject matter discloses the synthesis, in vitro validation, and methods of using a red-shifted fluorescent substrate of ALDH for labeling viable ALDHpos cells, isolating ALDHhi human hematopoietic stems cells, and fractionating ALDHpos cells in the presence of green fluorophores.

ALDH has been studied as a marker for normal and cancer stem cells. For example, ALDH1 has been identified as a marker used to isolate cancer stem cells of various human malignancies including bladder, breast, cervical, colon, head and neck, liver, lung, pancreas, prostate, and ovary (Ma and Allan, 2011). Further, Aldh1a1 and Aldh3a1 have been implicated in the protection of stem cells from cytotoxic drugs. ALDH$^{pos}$ stem cells also have been used as resources for regenerative (see, e.g., Balber, 2011). Furthermore, the presence of ALDH$^{int}$ leukemic stem cells can be used as a predictor for relapse after therapy (Gerber, et al., 2012).

Detectable ALDH substrates allow those cells expressing ALDH (e.g., certain types of stem cells) in a mixed population to be distinguished from those cells that do not express ALDH (See, for example, U.S. Pat. Nos. 5,876,956, and 6,991,897, each of which is incorporated by reference in its entirety). The substrates also can allow cells that express ALDH to a high degree to be distinguished from cells that express it to a smaller degree.

Accordingly, as provided in more detail herein below, the presently disclosed subject matter provides a red-shifted fluorescent substrate for ALDH, e.g., in some embodiments, AldeRed 588-A, for labeling viable ALDHpos cells. The presently disclosed subject matter further demonstrates that the red-shifted fluorescent substrates for ALDH disclosed herein can be used to isolate ALDHhi human hematopoietic stem cells from heterogeneous cord blood mononuclear cells. Further, the presently disclosed red-shifted fluorescent substrates for ALDH can be used for multi-color applications to fractionate ALDHpos cells in the presence of green fluorophores including the ALDEFLUOR™ reagent and cells expressing eGFP. The presently disclosed red-shifted fluorescent substrates for ALDH stain ALDHpos murine pancreatic centroacinar and terminal duct cells, as visualized by fluorescent microscopy. Accordingly, the presently disclosed red-shifted fluorescent substrates for ALDH provide a useful tool to select stem cells or study ALDH within a green fluorescent background.

More particularly, the presently disclosed red-shifted fluorescent substrates for ALDH can be used in a method for identifying intact, viable cells within a cell mixture that express an intracellular marker, for example, in some embodiments, an enzyme, such as cytosolic ALDH. The intracellular marker reacts with a cell-permeable fluorescent aldehyde to render the fluorescent aldehyde polar, and, hence, non-permeable to the cell membrane.

Accordingly, in some embodiments, the presently disclosed method comprises contacting a cell mixture with a cell-permeable, non-polar fluorescent aldehyde that is rendered polar by contact with the intracellular marker, for instance by oxidation. Once rendered polar, the fluorescent aldehyde is no longer permeable to the cell membrane and is trapped within only those cells in the cell mixture that express the intracellular marker. Cells containing the trapped polar, non-permeable fluorescent aldehyde can be identified by fluorescence techniques and equipment known in the art. Cell populations enriched in cells containing the polar fluorescent aldehyde can be obtained using cell sorting techniques, preferably automated fluorescence cell sorting techniques that separate cells containing or having attached thereto a fluorescent marker, such as Fluorescence Activated Cell Sorting (FACS).

The extent to which the substrate accumulates within a given cell can be related to the extent to which that cell expresses ALDH. All other things being equal, a cell expressing more ALDH will accumulate more.

The method for identifying cells containing cytosolic ALDH in intact, viable cells can provide a cell population enriched in hematopoietic stem cells, in some embodiments, a cell suspension of pluripotent hematopoietic stem cells (pluripotent HSC), that is substantially free of lineage-committed cells. By definition "pluripotent" hematopoietic stem cells are those progenitor cells having the ability to repopulate all hematopoietic lineages on a long-term basis. Further discussion of isolation of pluripotent hematopoietic stem cells can be found, for example, in U.S. Pat. Nos. 5,876,956 and 6,991,897, each of which is incorporated by reference in its entirety; and in Rovira et al., 2010; Storms et al., 1999; and Ma and Allan, 2011.

The ALDEFLUOR™ reagent (Aldagen Inc., Durham, N.C.) provides one method for identifying viable ALDH$^{pos}$ cells. Although very sensitive and specific for staining viable ALDH$^{Pos}$ cells, because it emits in the green region of the electromagnetic spectrum (512 nm), the ALDEFLUOR™ reagent cannot be simultaneously utilized in cells or animals expressing green fluorescent proteins. In addition, many cells demonstrate autofluorescence in this region of the spectrum (Shapiro, 2003), adding to the difficulty of isolating populations of true ALDH$^{pos}$ cells.

Accordingly, the presently disclosed subject matter provides detectable ALDH substrates, in particular ALDH substrates that have excitation and/or emission profiles that do not overlap significantly with the excitation and/or emission profile of green fluorescent protein.

In some embodiments, the presently disclosed subject matter provides a detectable substrate for ALDH, the substrate comprising a compound of formula (I):

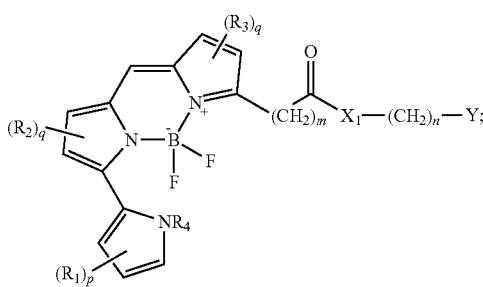

wherein: m and n are each independently an integer selected from the group consisting of 1, 2, 3, 4, 5, 6, 7, and 8; p is an integer selected from the group consisting of 0, 1, 2, and 3; each q is independently an integer selected from the group consisting of 0, 1, and 2; each $R_1$, $R_2$, and $R_3$ is independently selected from the group consisting of H, halogen, —OH, nitro, cyano, —O-alkyl, alkyl, alkenyl, alkynyl, cycloalkyl, heterocycloalkyl, cycloalkenyl, heterocycloalkenyl, aryl, or heteroaryl, optionally substituted by one to five substituents selected from H, halogen, alkyl, alkenyl, alkynyl, cycloalkyl, cycloalkenyl, heterocycloalkyl, heterocycloalkenyl, —OH, —O-alkyl, nitro, cyano, aryl, or heteroaryl; $R_4$ is selected from the group consisting of H, alkyl, alkoxyl, cycloalkyl, cycloheteroalkyl, aryl, and heteroaryl; $X_1$ is selected from the group consisting of $NR_5$, O, and S, wherein $R_5$ is selected from the group consisting of H, alkyl, alkoxyl, and aryl; Y is selected from the group consisting of —CH(=O); C(=O)—O$^-$; and —CH(OCH$_2$CH$_3$)$_2$; and wherein the compound of formula (I) has a peak emission wavelength of 530 nm or greater.

In some embodiments, the fluorescent moiety has a peak emission wavelength toward the red end of the spectrum, such as, for example, of about 530 nm or greater. The fluorescent moiety can have a peak emission wavelength of about 530 nm or greater; about 550 nm or greater; about 575 nm or greater; about 600 nm or greater; about 650 nm or greater; about 700 nm or greater; about 750 nm or greater; or about 800 nm or greater. In some cases, the fluorescent moiety can have a peak emission wavelength in the near infrared, for example, from about 800 nm or greater.

In some embodiments, the fluorescent moiety has fluorescence properties including emission and/or excitation wavelengths and characteristics that allow it to be readily distinguished from the fluorescence of other fluorescing moieties that may be present, for example, green fluorescent protein (GFP). For example, the fluorescent moiety can have excitation and emission wavelengths that are longer than that of the excitation and emission wavelengths, respectively, of GFP. In another example, the fluorescent moiety can have an excitation wavelength comparable to that of GFP (e.g., having overlapping excitation profiles), but the fluorescent moiety can have an emission wavelength longer than that of GFP, such that the different emissions can be readily distinguished.

Examples of suitable fluorescent moieties include, but are not limited to: BODIPY and analogous moieties; fluorescein and analogous moieties; rhodamine and analogous moieties; Alexa dyes and analogous moieties; cyanine dyes and analogous moieties; ASP dyes and analogous moieties (see, e.g., Stevens et al., 1993; and Wuskell et al., 2006); and cyanine and other fluorescent moieties. A variety of suitable fluorescent moieties are described in, for example, The Molecular Probes Handbook—A Guide to Fluorescent Probes and Labeling Technologies, 11th ed.

In some embodiments, the fluorescent moiety is a boron-dipyrromethene (BODIPY) dye. BODIPY dyes comprise a dipyrromethene ring structure complexed with a disubstituted boron atom. The core structure of a BODIPY dye, 4,4-difluoro-4-bora-3a,4a-diaza-s-indacene, is presented immediately herein below:

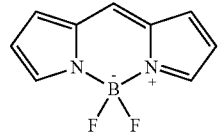

In the case of a BODIPY dye, the dipyrromethene group can be, in some embodiments, substituted with one or more groups that provide extended pi-conjugation. Extended pi-conjugation can provide BODIPY dyes with longer fluorescence emission wavelengths to provide for distinction from other fluorescing species. Such substituents can include, without limitation, alkenyl groups, alkynyl groups, aryl groups, and heteroaryl groups. In some embodiments, these groups can be combined to further extend the pi-conjugation, e.g., where the dipyrromethene group is substituted with styryl.

Representative BODIPY® dyes suitable for use with the presently disclosed subject matter include, but are not limited to, BODIPY® 530/550, SE (4,4-Difluoro-5,7-Diphenyl-4-Bora-3a,4a-Diaza-s-Indacene-3-Propionic Acid, Succinimidyl Ester); BODIPY® 558/568, SE (4,4-Difluoro-5-(2-Thienyl)-4-Bora-3a,4a-Diaza-s-Indacene-3-Propionic Acid, Succinimidyl Ester); BODIPY® 576/589, SE (4,4-Difluoro-5-(2-Pyrrolyl)-4-Bora-3a,4a-Diaza-s-Indacene-3-Propionic Acid, Succinimidyl Ester); BODIPY® 581/591, SE (4,4-Difluoro-5-(4-Phenyl-1,3-Butadienyl)-4-Bora-3a,4a-Diaza-s-Indacene-3-Propionic Acid, Succinimidyl Ester); BODIPY® TR-X, SE (6-(((4-(4,4-Difluoro-5-(2-Thienyl)-4-Bora-3a,4a-Diaza-s-Indacene-3-yl)phenoxy) acetyl)amino)hexanoic Acid, Succinimidyl Ester); BODIPY® TMR-X, SE (6-((4,4-Difluoro-1,3-Dimethyl-5-(4-Methoxyphenyl)-4-Bora-3a,4a-Diaza-s-Indacene-2-Propionyl)amino)hexanoic Acid, Succinimidyl Ester);

BODIPY® R6G, SE (4,4-Difluoro-5-Phenyl-4-Bora-3a,4a-Diaza-s-Indacene-3-Propionic Acid, Succinimidyl Ester); BODIPY® 630/650 Succinimidyl Ester (6-(((4,4-Difluoro-5-(2-Thienyl)-4-Bora-3a,4a-Diaza-s-Indacene-3-yl)styryloxy)acetyl)aminohexanoic Acid, Succinimidyl Ester)); BODIPY® 650/665-X, SE (6-(((4,4-Difluoro-5-(2-Pyrrolyl)-4-Bora-3a,4a-Diaza-s-Indacene-3-yl)Styryloxy)Acetyl) Aminohexanoic Acid, Succinimidyl Ester), available from Life Technologies™, Grand Island, N.Y. Note the designation, for example, 630/650 relates to the excitation wavelength (e.g., 630)/emission wavelength (e.g., 650).

Accordingly, in some embodiments, the fluorescent moiety can have the formula:

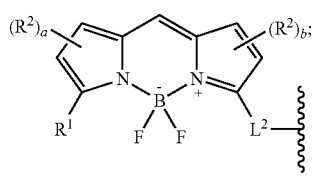

wherein: $L^2$ can be a bond or a conjugated alkenylene, alkynylene, cycloalkenylene, heterocycloalkenylene, arylene, or heteroarylene group; $R^1$ can be a conjugated alkenyl, alkynyl, cycloalkenyl, heterocycloalkenyl, aryl, or heteroaryl group, wherein $R^1$ can be optionally substituted by one to five substituents selected from H, halogen, alkyl, alkenyl, alkynyl, cycloalkyl, cycloalkenyl, heterocycloalkyl, heterocycloalkenyl, —OH, —O-alkyl, nitro, cyano, aryl, or heteroaryl; each $R^2$, individually, can be $R^1$, H, halogen, —OH, nitro, cyano, alkyl, alkenyl, alkynyl, cycloalkyl, heterocycloalkyl, —O-alkyl, aryl, or heteroaryl; a can be 0, 1, or 2; and b can be 0, 1, or 2.

In some embodiments, $R^1$ can be —(CH═CH)$_c$—Ar, where Ar is aryl or heteroaryl and c can be 0, 1, or 2. Ar can be optionally substituted phenyl, optionally substituted pyrrol-2-yl, optionally substituted furan-2-yl, or optionally substituted thiophene-2-yl. In some aspects, each $R^2$ can be H, and $R^1$ can be:

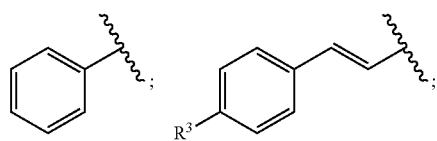

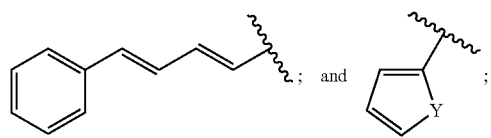

where $R^3$ is H or —OCH$_3$, and Y is O, NH, or S.

In some cases, $L^1$ can be —CH$_2$CH$_2$— and X can be O.

In some embodiments, the compound of formula (I) has the formula:

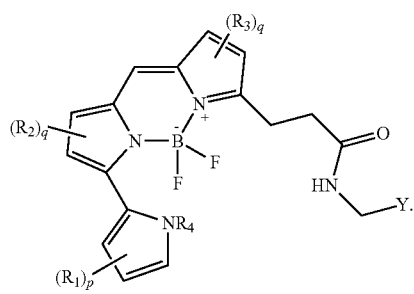

In particular embodiments, the compound of formula (I) is selected from the group consisting of:

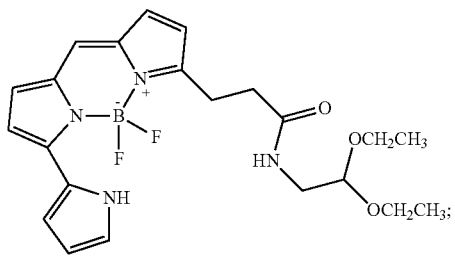

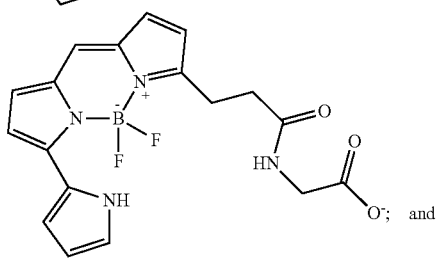

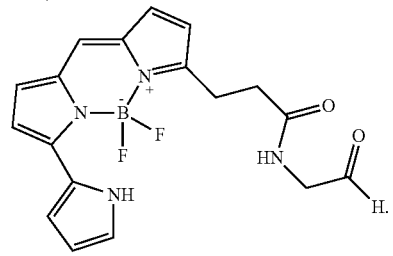

In yet more particular embodiments, the compound of formula (I) has the structure:

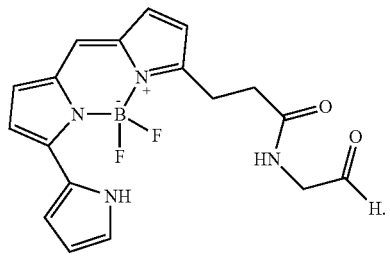

In some embodiments, a detectable substrate can be prepared according to the following general scheme, wherein $L^1$ is a linker moiety; and Ⓕ is a fluorescent moiety:

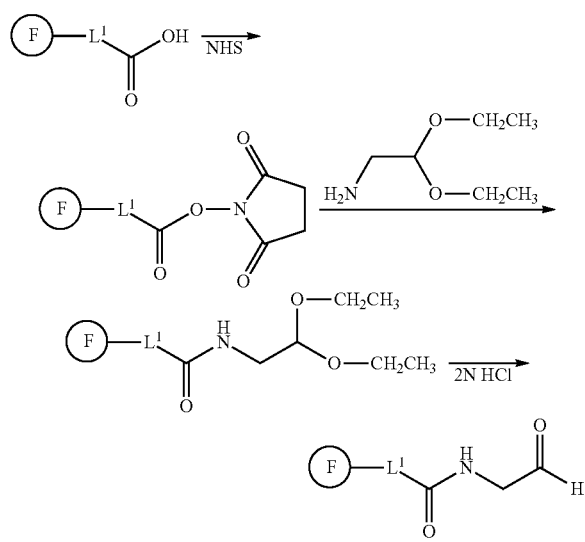

Stem cells generally express one or more active multi-drug efflux pumps, such as ABCB1 and/or ABCG2. The detectable ALDH substrate also may be a substrate for those pumps. Thus, even though ALDH substrates are converted into polar form (e.g., carboxylic acid form), the pumps can remove the converted ALDH from the cell, contrary to the desired accumulation of the converted ALDH substrate within ALDH$^{pos}$ cells. It can therefore be desirable, when assaying cells for ALDH activity, to include an inhibitor of one or more multi-drug efflux pumps. For example, the commercial Aldefluor® assay buffer contains verapamil, a pump inhibitor (see also U.S. Pat. No. 6,991,897, which is incorporated by reference in its entirety). Verapamil is an inhibitor of ABCB1, but does not inhibit ABCG2. Even in the presence of verapamil, cells that do accumulate the converted substrate can exhibit gradual decrease of fluorescent intensity over time (e.g., on the order of 1 hour). Inhibiting both pumps can enhance the accumulation of the converted inhibitor in ALDH$^{pos}$ cells, so that identification of ALDH$^{pos}$ cells is more effective than when no inhibitor, or an inhibitor of only one pump, is present.

Therefore it can be advantageous to carry out assays for ALDH$^{pos}$ cells in the presence of an inhibitor of ABCB1, an inhibitor of ABCG2, or, in some embodiments, in the presence of both an inhibitor of ABCB1 and an inhibitor of ABCG2, or, in other embodiments, the presence of a dual-activity inhibitor of ABCB1 and ABCG2, i.e., a single compound that inhibits both ABCB1 and ABCG2. Inhibitors of ABCB1, including verapamil, are known. Some inhibitors of ABCG2 are described in, for example, Zhang, et al., 2009. Dual action inhibitors, i.e., that inhibit both ABCB1 and ABCG2, include Galfenine, doxazosin mesylate, clebopride maleate, and flavoxate hydrochloride. Inhibitors of ABCG2 (but not ABCB1) include: fumitremorgin C (FTC), Ko143, Gefitinib, Harmine, Prazosin, Dipyridamole, Curcumin, Nelfinavir mesylate, Niguldipine, Riboflavin, Reserpine, Hesperetin, Tracazolate, Verteporfin, Quinacrine, Metyrapone, Rotenone, Acepromazine, Flutamide, *Podophyllum* resin, Piperacetazine, Acetophenazine maleate, and Raloxifene hydrochloride.

II. Pharmaceutical Compositions and Administration

In another aspect, the present disclosure provides a pharmaceutical composition including a compound of formula (I) alone or in combination with one or more additional therapeutic agents in admixture with a pharmaceutically acceptable excipient. One of skill in the art will recognize that the pharmaceutical compositions include the pharmaceutically acceptable salts of the compounds described above.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein.

In general, the "effective amount" of an active agent refers to the amount necessary to elicit the desired biological response. As will be appreciated by those of ordinary skill in this art, the effective amount of an agent or device may vary depending on such factors as the desired biological endpoint, the agent to be delivered, the biological target, and the like.

Pharmaceutically acceptable salts are generally well known to those of ordinary skill in the art, and may include, by way of example but not limitation, acetate, benzenesulfonate, besylate, benzoate, bicarbonate, bitartrate, bromide, calcium edetate, carnsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington: The Science and Practice of Pharmacy (20$^{th}$ ed.) Lippincott, Williams & Wilkins (2000). Pharmaceutically acceptable salts include, for example, acetate, benzoate, bromide, carbonate, citrate, gluconate, hydrobromide, hydrochloride, maleate, mesylate, napsylate, pamoate (embonate), phosphate, salicylate, succinate, sulfate, or tartrate.

Depending on the specific conditions being treated or diagnosed, such agents may be formulated into a liquid for administration. Techniques for formulation and administration may be found in Remington: The Science and Practice of Pharmacy (20$^{th}$ ed.) Lippincott, Williams & Wilkins (2000). Suitable routes of administration include direct intravenous (IV) administration.

For example, the agents of the disclosure may be formulated and diluted in aqueous solutions, such as in physiologically compatible buffers such as Hank's solution, Ringer's solution, or physiological saline buffer. Use of pharmaceutically acceptable inert carriers to formulate the compounds herein disclosed for the practice of the disclosure into dosages suitable for administration is within the scope of the disclosure. With proper choice of carrier and suitable manufacturing practice, the compositions of the present disclosure, in particular, those formulated as solutions. In addition to the active ingredients, these pharmaceutical compositions may contain suitable pharmaceutically acceptable carriers comprising excipients and auxiliaries which facilitate processing of the active compounds into preparations that can be used pharmaceutically.

III. Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

While the following terms in relation to compounds of formula (I) are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

The terms substituted, whether preceded by the term "optionally" or not, and substituent, as used herein, refer to the ability, as appreciated by one skilled in this art, to change one functional group for another functional group provided that the valency of all atoms is maintained. When more than one position in any given structure may be substituted with more than one substituent selected from a specified group, the substituent may be either the same or different at every position. The substituents also may be further substituted (e.g., an aryl group substituent may have another substituent off it, such as another aryl group, which is further substituted, for example, with fluorine at one or more positions).

Where substituent groups or linking groups are specified by their conventional chemical formulae, written from left to right, they equally encompass the chemically identical substituents that would result from writing the structure from right to left, e.g., —$CH_2O$— is equivalent to —$OCH_2$—; —C(=O)O— is equivalent to —OC(=O)—; —OC(=O) NR— is equivalent to —NRC(=O)O—, and the like.

When the term "independently selected" is used, the substituents being referred to (e.g., R groups, such as groups $R_1$, $R_2$, and the like, or variables, such as "m" and "n"), can be identical or different. For example, both $R_1$ and $R_2$ can be substituted alkyls, or $R_1$ can be hydrogen and $R_2$ can be a substituted alkyl, and the like.

The terms "a," "an," or "a(n)," when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

A named "R" or group will generally have the structure that is recognized in the art as corresponding to a group having that name, unless specified otherwise herein. For the purposes of illustration, certain representative "R" groups as set forth above are defined below.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term hydrocarbon, as used herein, refers to any chemical group comprising hydrogen and carbon. The hydrocarbon may be substituted or unsubstituted. As would be known to one skilled in this art, all valencies must be satisfied in making any substitutions. The hydrocarbon may be unsaturated, saturated, branched, unbranched, cyclic, polycyclic, or heterocyclic. Illustrative hydrocarbons are further defined herein below and include, for example, methyl, ethyl, n-propyl, iso-propyl, cyclopropyl, allyl, vinyl, n-butyl, tert-butyl, ethynyl, cyclohexyl, methoxy, diethylamino, and the like.

The term "alkyl," by itself or as part of another substituent, means, unless otherwise stated, a straight (i.e., unbranched) or branched chain, acyclic or cyclic hydrocarbon group, or combination thereof, which may be fully saturated, mono- or polyunsaturated and can include di- and multivalent groups, having the number of carbon atoms designated (i.e., $C_1$-$C_{10}$ means one to ten carbons). In particular embodiments, the term "alkyl" refers to $C_{1-20}$ inclusive, linear (i.e., "straight-chain"), branched, or cyclic, saturated or at least partially and in some cases fully unsaturated (i.e., alkenyl and alkynyl) hydrocarbon radicals derived from a hydrocarbon moiety containing between one and twenty carbon atoms by removal of a single hydrogen atom.

Representative saturated hydrocarbon groups include, but are not limited to, methyl, ethyl, n-propyl, isopropyl, n-butyl, isobutyl, sec-butyl, tert-butyl, n-pentyl, sec-pentyl, isopentyl, neopentyl, n-hexyl, sec-hexyl, n-heptyl, n-octyl, n-decyl, n-undecyl, dodecyl, cyclohexyl, (cyclohexyl)methyl, cyclopropylmethyl, and homologs and isomers thereof.

"Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "heteroalkyl," by itself or in combination with another term, means, unless otherwise stated, a stable straight or branched chain, or cyclic hydrocarbon group, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —$CH_2$—$CH_2$—O—$CH_3$, —$CH_2$—$CH_2$—NH—$CH_3$, —CH$_2$—CH$_2$—N(CH$_3$)—CH$_3$, —CH$_2$—S—CH$_2$—CH$_3$, —CH$_2$—CH$_{2S}$—S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, 0-CH$_3$, -0-CH$_2$—CH$_3$, and —CN. Up to two or three heteroatoms may be consecutive, such as, for example, —CH$_2$—NH—OCH$_3$ and —CH$_2$—O—Si(CH$_3$)$_3$.

As described above, heteroalkyl groups, as used herein, include those groups that are attached to the remainder of the molecule through a heteroatom, such as —C(O)R', —C(O)NR', —NR'R", —OR', —SR, and/or —SO$_2$R'. Where "heteroalkyl" is recited, followed by recitations of specific heteroalkyl groups, such as —NR'R or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl, and fused ring systems, such as dihydro- and tetrahydronaphthalene, and the like.

The term "cycloalkylalkyl," as used herein, refers to a cycloalkyl group as defined hereinabove, which is attached to the parent molecular moiety through an alkyl group, also as defined above. Examples of cycloalkylalkyl groups include cyclopropylmethyl and cyclopentylethyl.

The terms "cycloheteroalkyl" or "heterocycloalkyl" refer to a non-aromatic ring system, unsaturated or partially unsaturated ring system, such as a 3- to 10-member substituted or unsubstituted cycloalkyl ring system, including one or more heteroatoms, which can be the same or different, and are selected from the group consisting of nitrogen (N), oxygen (O), sulfur (S), phosphorus (P), and silicon (Si), and optionally can include one or more double bonds.

The cycloheteroalkyl ring can be optionally fused to or otherwise attached to other cycloheteroalkyl rings and/or non-aromatic hydrocarbon rings. Heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocyclic refers to a non-aromatic 5-, 6-, or 7-membered ring or a polycyclic group wherein at least one ring atom is a heteroatom selected from O, S, and N (wherein the nitrogen and sulfur heteroatoms may be optionally oxidized), including, but not limited to, a bi- or tri-cyclic group, comprising fused six-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Representative cycloheteroalkyl ring systems include, but are not limited to pyrrolidinyl, pyrrolinyl, imidazolidinyl, imidazolinyl, pyrazolidinyl, pyrazolinyl, piperidyl, piperazinyl, indolinyl, quinuclidinyl, morpholinyl, thiomorpholinyl, thiadiazinanyl, tetrahydrofuranyl, and the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. Alkyl groups which are limited to hydrocarbon groups are termed "homoalkyl."

More particularly, the term "alkenyl" as used herein refers to a monovalent group derived from a C$_{1-20}$ inclusive straight or branched hydrocarbon moiety having at least one carbon-carbon double bond by the removal of a single hydrogen atom. Alkenyl groups include, for example, ethenyl (i.e., vinyl), propenyl, butenyl, 1-methyl-2-buten-1-yl, pentenyl, hexenyl, octenyl, and butadienyl.

The term "cycloalkenyl" as used herein refers to a cyclic hydrocarbon containing at least one carbon-carbon double bond. Examples of cycloalkenyl groups include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "alkynyl" as used herein refers to a monovalent group derived from a straight or branched C$_{1-20}$ hydrocarbon of a designed number of carbon atoms containing at least one carbon-carbon triple bond. Examples of "alkynyl" include ethynyl, 2-propynyl (propargyl), 1-propynyl, pentynyl, hexynyl, heptynyl, and allenyl groups, and the like.

The term "alkylene" by itself or a part of another substituent refers to a straight or branched bivalent aliphatic hydrocarbon group derived from an alkyl group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—CH$_2$—); ethylene (—CH$_2$—CH$_2$—); propylene (—(CH$_2$)$_3$—); cyclohexylene (—C$_6$H$_{10}$—); —CH=CH—CH=CH—; —CH=CH—CH$_2$—; —CH$_2$CH$_2$CH$_2$CH$_2$—, —CH$_2$CH=CHCH$_2$—, —CH$_2$CsCCH$_2$—, —CH$_2$CH$_2$CH (CH$_2$CH$_2$CH$_3$)CH$_2$—, —(CH$_2$)$_q$—N(R)—(CH$_2$)$_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxy (—O—CH$_2$—O—); and ethylenedioxy (—O—(CH$_2$)$_2$—O—). An alkylene group can have about 2 to about 3 carbon atoms and can further have 6-20 carbons. Typically, an alkyl (or alkylene) group will have from 1 to 24 carbon atoms, with those groups having 10 or fewer carbon atoms being some embodiments of the present disclosure. A "lower alkyl" or "lower alkylene" is a shorter chain alkyl or alkylene group, generally having eight or fewer carbon atoms.

The term "heteroalkylene" by itself or as part of another substituent means a divalent group derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—.

The term "aryl" means, unless otherwise stated, an aromatic hydrocarbon substituent that can be a single ring or multiple rings (such as from 1 to 3 rings), which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent forms of aryl and heteroaryl, respectively.

For brevity, the term "aryl" when used in combination with other terms (e.g., aryloxo, arylthioxo, arylalkyl) includes both aryl and heteroaryl rings as defined above. Thus, the terms "arylalkyl" and "heteroarylalkyl" are meant to include those groups in which an aryl or heteroaryl group is attached to an alkyl group (e.g., benzyl, phenethyl, pyridylmethyl, furylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). However, the term "haloaryl," as used herein is meant to cover only aryls substituted with one or more halogens.

Where a heteroalkyl, heterocycloalkyl, or heteroaryl includes a specific number of members (e.g. "3 to 7 membered"), the term "member" refers to a carbon or heteroatom.

Further, a structure represented generally by the formula:

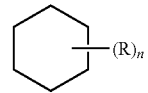

as used herein refers to a ring structure, for example, but not limited to a 3-carbon, a 4-carbon, a 5-carbon, a 6-carbon, a 7-carbon, and the like, aliphatic and/or aromatic cyclic compound, including a saturated ring structure, a partially saturated ring structure, and an unsaturated ring structure, comprising a substituent R group, wherein the R group can be present or absent, and when present, one or more R groups can each be substituted on one or more available carbon atoms of the ring structure. The presence or absence of the R group and number of R groups is determined by the value of the variable "n," which is an integer generally having a value ranging from 0 to the number of carbon atoms on the ring available for substitution. Each R group, if more than one, is substituted on an available carbon of the ring structure rather than on another R group. For example, the structure above where n is 0 to 2 would comprise compound groups including, but not limited to:

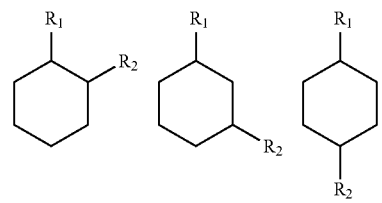

and the like.

A dashed line representing a bond in a cyclic ring structure indicates that the bond can be either present or absent in the ring. That is, a dashed line representing a bond in a cyclic ring structure indicates that the ring structure is selected from the group consisting of a saturated ring structure, a partially saturated ring structure, and an unsaturated ring structure.

The symbol ( ⁓⁓⁓ ) denotes the point of attachment of a moiety to the remainder of the molecule.

When a named atom of an aromatic ring or a heterocyclic aromatic ring is defined as being "absent," the named atom is replaced by a direct bond.

Each of above terms (e.g., "alkyl," "heteroalkyl," "cycloalkyl, and "heterocycloalkyl", "aryl," "heteroaryl," "phosphonate," and "sulfonate" as well as their divalent derivatives) are meant to include both substituted and unsubstituted forms of the indicated group. Optional substituents for each type of group are provided below.

Substituents for alkyl, heteroalkyl, cycloalkyl, heterocycloalkyl monovalent and divalent derivative groups (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R"', —OC(O)R', —C(O)R', —CO$_2$R', —C(O)NR'R", —OC(O)NR'R", —NR"C(O)R', —NR'—C(O)NR"R"', —NR"C(O)OR', —NR—C(NR'R")=NR"', —S(O)R', —S(O)$_2$R', —S(O)$_2$NR'R", —NRSO$_2$R', —CN and —NO$_2$ in a number ranging from zero to (2m'+1), where m' is the total number of carbon atoms in such groups. R', R", R"' and R"" each may independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. As used herein, an "alkoxy" group is an alkyl attached to the remainder of the molecule through a divalent oxygen. When a compound of the disclosure includes more than one R group, for example, each of the R groups is independently selected as are each R', R'', R''' and R'''' groups when more than one of these groups is present. When R' and R'' are attached to the same nitrogen atom, they can be combined with the nitrogen atom to form a 4-, 5-, 6-, or 7-membered ring. For example, —NR'R'' is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for alkyl groups above, exemplary substituents for aryl and heteroaryl groups (as well as their divalent derivatives) are varied and are selected from, for example: halogen, —OR', —NR'R'', —SR', -halogen, —SiR'R''R''', —OC(O)R', —C(O)R', —CO$_2$R', —C(O)NR'R'', —OC(O)NR'R'', —NR''C(O)R', —NR'—C(O)NR''R''', —NR''C(O)OR', —NR—C(NR'R''R''')=NR'''', —NR—C(NR'R'')=NR'''—S(O)R', —S(O)$_2$R', —S(O)$_2$NR'R'', —NRSO$_2$R', —CN and —NO$_2$, —R', —N$_3$, —CH(Ph)$_2$, fluoro(C$_1$-C$_4$)alkoxo, and fluoro (C$_1$-C$_4$)alkyl, in a number ranging from zero to the total number of open valences on aromatic ring system; and where R', R'', R''' and R'''' may be independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R'', R''' and R'''' groups when more than one of these groups is present.

Two of the substituents on adjacent atoms of aryl or heteroaryl ring may optionally form a ring of the formula —T—C(O)—(CRR')$_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4.

One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C''R''')$_d$—, where s and d are independently integers of from 0 to 3, and X' is —O—, —NR'—, —S—, —S(O)—, —S(O)$_2$—, or —S(O)$_2$NR'—. The substituents R, R', R'' and R''' may be independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "acyl" refers to an organic acid group wherein the —OH of the carboxyl group has been replaced with another substituent and has the general formula RC(=O)—, wherein R is an alkyl, alkenyl, alkynyl, aryl, carbocylic, heterocyclic, or aromatic heterocyclic group as defined herein). As such, the term "acyl" specifically includes arylacyl groups, such as an acetylfuran and a phenacyl group. Specific examples of acyl groups include acetyl and benzoyl.

The terms "alkoxyl" or "alkoxy" are used interchangeably herein and refer to a saturated (i.e., alkyl-O—) or unsaturated (i.e., alkenyl-O— and alkynyl-O—) group attached to the parent molecular moiety through an oxygen atom, wherein the terms "alkyl," "alkenyl," and "alkynyl" are as previously described and can include C$_{1-20}$ inclusive, linear, branched, or cyclic, saturated or unsaturated oxo-hydrocarbon chains, including, for example, methoxyl, ethoxyl, propoxyl, isopropoxyl, n-butoxyl, sec-butoxyl, t-butoxyl, and n-pentoxyl, neopentoxyl, n-hexoxyl, and the like.

The term "alkoxyalkyl" as used herein refers to an alkyl-O-alkyl ether, for example, a methoxyethyl or an ethoxymethyl group.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl.

"Alkoxycarbonyl" refers to an alkyl-O—CO— group. Exemplary alkoxycarbonyl groups include methoxycarbonyl, ethoxycarbonyl, butyloxycarbonyl, and t-butyloxycarbonyl.

"Aryloxycarbonyl" refers to an aryl-O—CO— group. Exemplary aryloxycarbonyl groups include phenoxy- and naphthoxy-carbonyl.

"Aralkoxycarbonyl" refers to an aralkyl-O—CO— group. An exemplary aralkoxycarbonyl group is benzyloxycarbonyl.

"Carbamoyl" refers to an amide group of the formula —CONH$_2$. "Alkylcarbamoyl" refers to a R'RN—CO— group wherein one of R and R' is hydrogen and the other of R and R' is alkyl and/or substituted alkyl as previously described. "Dialkylcarbamoyl" refers to a R'RN—CO— group wherein each of R and R' is independently alkyl and/or substituted alkyl as previously described.

The term carbonyldioxyl, as used herein, refers to a carbonate group of the formula —O—CO—OR.

"Acyloxyl" refers to an acyl-O— group wherein acyl is as previously described.

The term "amino" refers to the —NH$_2$ group and also refers to a nitrogen containing group as is known in the art derived from ammonia by the replacement of one or more hydrogen radicals by organic radicals. For example, the terms "acylamino" and "alkylamino" refer to specific N-substituted organic radicals with acyl and alkyl substituent groups respectively.

An "aminoalkyl" as used herein refers to an amino group covalently bound to an alkylene linker. More particularly, the terms alkylamino, dialkylamino, and trialkylamino as used herein refer to one, two, or three, respectively, alkyl groups, as previously defined, attached to the parent molecular moiety through a nitrogen atom. The term alkylamino refers to a group having the structure —NHR' wherein R' is an alkyl group, as previously defined; whereas the term dialkylamino refers to a group having the structure —NR'R"R'", wherein R', R", and R"' are each independently selected from the group consisting of alkyl groups. The term trialkylamino refers to a group having the structure —NR'R"R'", wherein R', R", and R"' are each independently selected from the group consisting of alkyl groups. Additionally, R', R", and/or R"' taken together may optionally be —(CH$_2$)$_k$— where k is an integer from 2 to 6. Examples include, but are not limited to, methylamino, dimethylamino, ethylamino, diethylamino, diethylaminocarbonyl, methylethylamino, iso-propylamino, piperidino, trimethylamino, and propylamino.

The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

The terms alkylthioether and thioalkoxyl refer to a saturated (i.e., alkyl-S—) or unsaturated (i.e., alkenyl-S— and alkynyl-S—) group attached to the parent molecular moiety through a sulfur atom. Examples of thioalkoxyl moieties include, but are not limited to, methylthio, ethylthio, propylthio, isopropylthio, n-butylthio, and the like.

"Acylamino" refers to an acyl-NH— group wherein acyl is as previously described. "Aroylamino" refers to an aroyl-NH— group wherein aroyl is as previously described.

The term "carbonyl" refers to the —(C=O)— group.

The term "carboxyl" refers to the —COOH group. Such groups also are referred to herein as a "carboxylic acid" moiety.

The terms "halo," "halide," or "halogen" as used herein refer to fluoro, chloro, bromo, and iodo groups. Additionally, terms such as "haloalkyl," are meant to include monohaloalkyl and polyhaloalkyl. For example, the term "halo(C$_1$-C$_4$)alkyl" is mean to include, but not be limited to, trifluoromethyl, 2,2,2-trifluoroethyl, 4-chlorobutyl, 3-bromopropyl, and the like.

The term "hydroxyl" refers to the —OH group.

The term "hydroxyalkyl" refers to an alkyl group substituted with an —OH group.

The term "mercapto" refers to the —SH group.

The term "oxo" as used herein means an oxygen atom that is double bonded to a carbon atom or to another element.

The term "nitro" refers to the —NO$_2$ group.

The term "thio" refers to a compound described previously herein wherein a carbon or oxygen atom is replaced by a sulfur atom.

The term "sulfate" refers to the —SO$_4$ group.

The term thiohydroxyl or thiol, as used herein, refers to a group of the formula —SH.

The term ureido refers to a urea group of the formula —NH—CO—NH$_2$.

Unless otherwise explicitly defined, a "substituent group," as used herein, includes a functional group selected from one or more of the following moieties, which are defined herein:

(A) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "lower substituent" or "lower substituent group," as used herein means a group selected from all of the substituents described hereinabove for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_5$-C$_7$ cycloalkyl, and each substituted or unsubstituted heterocycloalkyl is a substituted or unsubstituted 5 to 7 membered heterocycloalkyl.

A "size-limited substituent" or "size-limited substituent group," as used herein means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_4$-C$_8$ cycloalkyl, and each substituted or unsubstituted heterocycloalkyl is a substituted or unsubstituted 4 to 8 membered heterocycloalkyl.

Throughout the specification and claims, a given chemical formula or name shall encompass all tautomers, congeners, and optical- and stereoisomers, as well as racemic mixtures where such isomers and mixtures exist.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those which are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefenic bonds or other centers of geometric asymmetry, and unless specified otherwise, it is intended that the compounds include both E and Z geometric isomers.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

It will be apparent to one skilled in the art that certain compounds of this disclosure may exist in tautomeric forms, all such tautomeric forms of the compounds being within the scope of the disclosure. The term "tautomer," as used herein, refers to one of two or more structural isomers which exist in equilibrium and which are readily converted from one isomeric form to another.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this disclosure.

The compounds of the present disclosure also may contain unnatural proportions of atomic isotopes at one or more of atoms that constitute such compounds. For example, the compounds may be radiolabeled with radioactive isotopes, such as for example tritium ($^{3}H$), iodine-125 ($^{125}I$) or carbon-14 ($^{14}C$). All isotopic variations of the compounds of the present disclosure, whether radioactive or not, are encompassed within the scope of the present disclosure.

The compounds of the present disclosure may exist as salts. The present disclosure includes such salts. Examples of applicable salt forms include hydrochlorides, hydrobromides, sulfates, methanesulfonates, nitrates, maleates, acetates, citrates, fumarates, tartrates (e.g. (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

The term "pharmaceutically acceptable salts" is meant to include salts of active compounds which are prepared with relatively nontoxic acids or bases, depending on the particular substituent moieties found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like {see, for example, Berge et al, "Pharmaceutical Salts", Journal of Pharmaceutical Science, 1977, 66, 1-19). Certain specific compounds of the present disclosure contain both basic and acidic functionalities that allow the compounds to be converted into either base or acid addition salts.

In addition to salt forms, the present disclosure provides compounds, which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

The term "protecting group" refers to chemical moieties that block some or all reactive moieties of a compound and prevent such moieties from participating in chemical reactions until the protective group is removed, for example, those moieties listed and described in T. W. Greene, P.G.M. Wuts, Protective Groups in Organic Synthesis, 3rd ed. John Wiley & Sons (1999). It may be advantageous, where different protecting groups are employed, that each (different) protective group be removable by a different means. Protective groups that are cleaved under totally disparate reaction conditions allow differential removal of such protecting groups. For example, protective groups can be removed by acid, base, and hydrogenolysis. Groups such as trityl, dimethoxytrityl, acetal and tert-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, without limitation, methyl, ethyl, and acetyl in the presence of amines blocked with acid labile groups such as tert-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a palladium(O)-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typical blocking/protecting groups include, but are not limited to the following moieties:

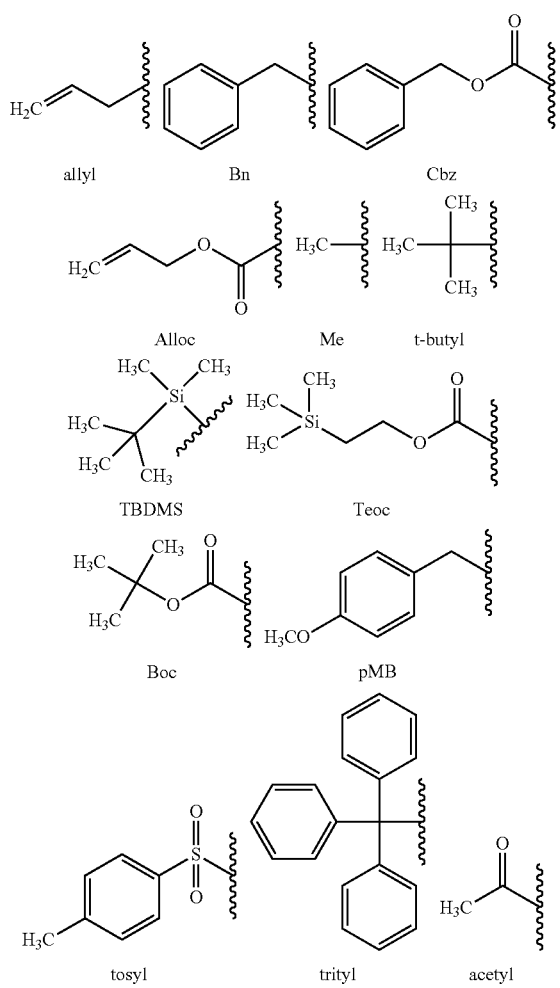

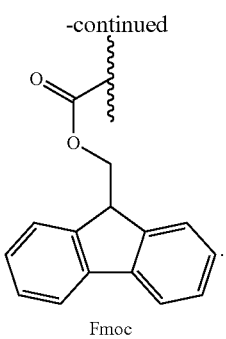

Fmoc

The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Methods

Cell Lines and Animals. The K562 human chronic myelogenous leukemia cell line was purchased from American Type Culture Collection (CLL-243™) and maintained in suspension in IMDM media supplemented with 10% FBS. The murine leukemia cell line L1210 (ALDH$^{low}$) and L1210/cpa (ALDH$^{hi}$) were provided by Dr. Richard J. Jones (Johns Hopkins University, Baltimore Md.) and maintained in suspension in RPMI 1640 supplemented with 10% FBS. All cells were grown at 37° C. in a humidified incubator with 5% $CO_2$. All animal experiments were performed in accordance with protocols approved by Johns Hopkins University Animal Care and Use Committee (ACUC).

Reagents and Analyses. BODIPY® 576/589 succinimidyl ester and BODIPY® 650/665 succinimidyl ester were purchased from Life Technologies Inc., (Grand Island, N.Y.). (E)-4-(4-(dimethylamino)styryl)-1-(3-isothiocyanatopropyl)pyridin-1-ium chloride 1 was synthesized analogously to the previously reported di-butyl analog. Hassner, A., et al., J Org. Chem. 49, 2546-2551 (1984). Chemicals and solvents for synthesis and high-performance liquid chromatography (HPLC) were acquired from Sigma-Aldrich (Milwaukee, Wis.) or Fisher Scientific (Pittsburgh, Pa.), and used without further purification. HPLC was performed on an Agilent Prostar System equipped with a 325 Variable wavelength detector and controlled by Galaxie Software using a Phenomenex 4.6×250 mm Luna C18, 10 micron column. AldeRed 493 aldehyde diethyl acetal (FIGS. 14a-14b) and AldeRed 493-A (FIGS. 14c-14d) were chromatographed using Method 1. AldeRed 588 aldehyde diethyl acetal (FIGS. 15a-15b), AldeRed 588-A (FIGS. 15c-15d), AldeRed 659 aldehyde diethyl acetal (FIGS. 16a-16b), AldeRed 659-A (FIGS. 16c-16d) were chromatographed using Method 2. Method 1: Solvent A: 100% water; Solvent B: 100% methanol; 0-5 min 100% A, 5-25 min linear gradient from 100% A to 100% B, 25-30 min 100% B, 30-35 min linear gradient from 100% B to 100% A, 35-38 min 100% A, 2 mL/min. Method 2: Solvent A: 100% water; Solvent B: 100% acetonitrile; 0-20 min linear gradient from 90% A/10% B to 10% A/90% B; 20-25 min 10% A/90% B, 25-30 min linear gradient from 10% A/90% B to 90% A/10% B, 2 mL/min. $^1$H-NMR spectra were obtained on a Bruker Avance 400 MHz Spectrometer. High resolution mass spectra were obtained by the University of Notre Dame Mass Spectrometry & Proteomics Facility (Notre Dame, Ind.) using ESI either by direct infusion on a Bruker micrOTOF-II or by LC elution via an ultra-high pressure Dionex® RSLC with C18 column coupled with a Bruker micrOTOF-Q II. The excitation and emission profiles of synthesized products were measured using a spectrofluorophotometer (Shimadzu, RF-5301pc, Columbia, Md.).

Synthesis of AldeRed 493 Amino Acetal Aldehyde Diethylacetal 4. Aminoacetaldehyde diethyl acetal (0.024 mmol, 3 μL) was added to a solution of (E)-4-(4-(dimethylamino)styryl)-1-(3-isothiocyanatopropyl)pyridin-1-ium chloride 1 (3.6 mg, 0.01 mmol in 1 mL of DMF) and 5 μL of triethylamine and mixed by stirring for 30 min in the dark. 5 mL of water was added and the resulting solution was extracted with ether (2×5 mL). Water in the aqueous phase was evaporated under vacuum and the residue was purified by passing through a small C18 column, eluted with 1:1 water/acetonitrile. Yield: 1.8 mg, 0.004 mmol, 40%. $^1$H NMR (400 MHz, DMSO-$d_6$): δ=1.10 (t, 6H, J=7.6 Hz); 2.09-2.13 (m, 2H); 3.0 (s, 6H); 3.4-3.5 (m, 6H); 3.55-3.62 (m, 2H); 4.43 (t, 2H, J=6.8 Hz); 4.5-4.6 (m, 1H); 6.77 (d, 2H, J=8.8 Hz); 7.15 (d, 1H, J=16.4 Hz); 7.58 (d, 2H, J=8.4 Hz); 7.90 (d, 1H, J=15.6 Hz); 8.04 (d, 2H, J=6.8 Hz); 8.74 (d, 2H, 6.8 Hz). HRESI-MS $C_{25}H_{37}N_4O_2S^+$ calcd 457.2632; found 457.2632 (FIG. 17a).

Synthesis of AldeRed 588 Aldehyde Diethyl Acetal 5. Aminoacetaldehyde diethyl acetal (0.024 mmol, 3 μL) was added to BODIPY® 576/589 succinimidyl ester 2 (5 mg, 0.012 mmol in 1 mL of THF) and mixed by stirring for 30 min in the dark. After evaporating THF, AldeRed 588 aldehyde diethyl acetal 5 was purified by flash column chromatography using ethyl acetate/hexane (1:1) as an eluent to give 3.8 mg, 0.0086 mmol 75% yield. $^1$H NMR (400 MHz, $CDCl_3$): δ=1.16 (t, 6H, J=7 Hz); 2.65 (t, 2H, J=7.2 Hz); 3.31 (t, 2H, J=7.2 Hz); 3.37 (t, 2H, J=5.6 Hz); 3.48 (m, 2H); 3.65 (m, 2H); 4.43 (t, 1H, 5.6 Hz); 5.82 (br, 1H); 6.27 (d, 1H, 3.6=3.6 Hz); 6.36 (br, 1H); 6.81 (d, 1H, J=4 Hz); 6.85 (d, 1H, 4.4 Hz); 6.96 (s, 1H); 6.97 (s, 1H), 7.02 (d, 1H, J=4.4 Hz); 7.16 (s, 1H). HRESI-MS $C_{22}H_{28}BF_2N_4O_3$ calcd 445.4222; found 445.4222 (FIG. 17b).

Synthesis of AldeRed 659 Aldehyde Diethyl Acetal 6. Aminoacetaldehyde diethyl acetal (0.016 mmol, 2 μL) was added to BODIPY® 650/665 succinimidyl ester 3 (5 mg, 0.0078 mmol in 1 mL of THF) and mixed by stirring for 30 min in the dark. After evaporating THF, AldeRed 659 aldehyde diethyl acetal 6 was purified by flash column chromatography using ethyl acetate/hexane (1:1) as an eluent to give 3.5 mg, 0.0053 mmol, 70% yield. $^1$H NMR (400 MHz, $CDCl_3$): δ=1.19 (t, 6H, J=7.8 Hz); 1.33-1.37 (m, 2H), 1.5-1.58 (m, 2H); 1.6-1.68 (m, 2H); 2.16 (t, 2H, J=7.8 Hz); 3.31-3.38 (m, 4H); 3.46-3.55 (m, 2H); 3.62-3.71 (m, 2H); 4.46 (t, 1H, J=5.2 Hz); 4.51 (s, 2H); 5.65 (br, 1H); 6.36-6.39 (m, 1H); 6.57-6.62 (m, 1H); 6.83-6.88 (m, 2H); 6.89 (d, 1H, J=4 Hz); 6.92-6.98 (m, 4H); 7.0 (d, 1H, J=4 Hz); 7.18 (m, 1H); 7.50-7.58 (m, 3H). HRESI-MS $C_{35}H_{43}BF_2N_5O_5$ calcd 662.3326; found: 662.3326 (FIG. 17c).

Preparation of Aldehyde Derivatives, AldeRed 493-A, AldeRed 588-A and AldeRed 659-A. All diethyl acetal precursors to the final aldehyde derivatives were dissolved in 100% DMSO at 5 mM and stored at −20° C. in stock solutions. Immediately before the assay a 25 µL aliquot of each stock solution was deprotected by adding the same volume of 2N HCl followed by incubation for 30 min at room temperature. The resulting reaction mixtures were neutralized by adding 350 µL of assay buffer (PBS supplemented with 1% FBS and 50 µM verapamil).

Isolation of AldeRed 588-A. To characterize AldeRed 588-A produced upon hydrolysis, AldeRed 588 aldehyde diethyl acetal 5 (0.5 mg in 300 µL) was mixed with 300 µL of 2N HCl and incubated for 30 min at room temperature. The reaction mixture was then diluted with 2 mL of water. The clear purple solution was injected into the HPLC. The purification of AldeRed-588A was performed using an Agilent 1260 infinity preparative HPLC system equipped with a Phenomenex Luna C18, 10 micron column and a flow rate of 10 mL/min. The desired product eluted at 3.3 min with acetonitrile/water (40/60) and collected. (The solvent front eluted at 1.1 min.) The collected fraction was frozen at −78'C immediately and lyophilized to dryness. Approximately 0.4 mg of AldeRed-588A was obtained as a dark powder. HRESI-MS $C_{18}H_{18}BF_2N_4O_2$ calcd 371.1485; found: 371.1489 (FIG. 18).

In Vitro Fluorescence Uptake Assay for ALDH Activity. One million cells were resuspended in assay buffer and 5 µL of the corresponding aldehyde (ALDEFLUOR™, AldeRed 493-A, AldeRed 588-A or AldeRed 659-A) was added to the suspension. In each case a 0.5 mL aliquot of the suspension was immediately added to a 5 mL polystyrene round bottom tube (BD Biosciences, San Jose, Calif.) containing 5 µL of diethylaminobenzaldehyde (DEAB) (STEMCELL Technologies, Inc., Vancouver, BC, Canada). Cells were incubated in a water bath at 37° C. for 30 min followed by washing with 4 mL of cold assay buffer once. Cells were resuspended in cold assay buffer (5×10⁵/200 µL) and stored on ice until analyzed. Stained cells were analyzed by FACS LSRII (BD Biosciences, San Jose, Calif.) equipped with four lasers (405 nm, 488 nm, 532 nm, and 633 nm) and 14 emission filters. All three candidate ALDH substrates were tested on all 15 filters. AldeRed 588-A was also tested on a FACSCALIBUR™ (BD Biosciences, San Jose, CA) with 488-nm blue laser and phycoerythrin (PE) filters.

Isolation of $ALDH^{hi}$ Human Hematopoietic Stem Cells (HSCs) from Heterogeneous Cord Blood Cells Using AldeRed 588-A. Frozen human cord blood mononuclear cells were purchased from ALLCELLS (Alamenda, Calif.). Cells were thawed according to the provider's instructions immediately before use followed by re-suspension in assay buffer (1×10⁶ cells/mL). The staining procedure for ALDEFLUOR™ and AldeRed 588-A was same as described above for the in vitro fluorescence uptake assay. $ALDH^{hi}$ cells were sorted into RPMI supplemented with 10% FBS using FACSARIA™ (BD Biosciences, San Jose, CA) equipped with four lasers (405 nm, 488 nm, 532 nm, and 633 nm) and 14 emission filters. Five hundred $ALDH^{hi}$ cells were plated in 1 mL of Methocult® H4435 (STEMCELL Technologies, Inc., Vancouver, BC, Canada) and incubated in a humidified incubator at 37° C. with an atmosphere of 5% $CO_2$ for one week. Colonies formed were counted one week later and photographed using a Nikon TE-200 inverted microscope.

Enrichment of HSCs from Bone Marrow Cells of TNR Mice. Transgenic notch reporter (TNR) mice [Tg(Cp-EGFP) 25Gaia] were provided by Dr. Shyam Biswal (Johns Hopkins School of Public Health). Bone marrow cells were harvested by repeatedly flushing the femur, tibia, and pelvis with a 26Gx5/8 needle. Red blood cells were depleted using RBC lysis buffer (BioLegend, San Diego, Calif.) according to the manufacturer's instructions. Cells were stained with AldeRed 588-A and sorted into five populations ($eGFP^{neg}/ALDH^{pos}$, $eGFP^{neg}/ALDH^{int}$, $eGFP^{neg}/ALDH^{hi}$, $eGFP^{pos}/ALDH^{int}$, and $eGFP^{pos}/ALDH^{hi}$) using FACSARIA™ (BD Biosciences, San Jose, Calif.) with fluorescein isothiocyanate (FITC) and PE-Texas Red® filters for eGFP and AldeRed 588-A, respectively. Twenty thousand cells from each population were plated in 1 mL of Methocult® M3434 (STEMCELL Technologies, Inc., Vancouver, BC, Canada) and incubated in a humidified incubator at 37° C. with and atmosphere of 5% $CO_2$ for one week. Colonies formed were counted one week later and photographed using a Nikon TE-200 inverted microscope. A mouse hematopoietic lineage cocktail (eFluor® 450, eBiosciences, San Diego, Calif.) containing anti-mouse Ly-6A/E (PE-Cy7, BioLegend, San Diego, Calif.), and anti-mouse CD117 (APC-Cy7, BioLegend, San Diego, Calif.) was used to stain and isolate lineage⁻/c-Kit⁺/Sca1⁺ (LKS) cells using LSR II.

Microscopic ALDH Staining of Murine Pancreatic Centoracinar and Terminal Duct (CA/TD) Cells. Mouse pancreatic acinar preparation was performed as previously described (Rovira et al., 2010). Briefly, adult CD1 mouse pancreas was harvested and digested in 1 mg/mL collagenase-P (Roche, Indianapolis, Ind.) at 37° C. in a water bath for 15 min. The collagenase-P reaction was terminated by the addition of ice cold HBSS with 5% FBS. Following multiple washes, collagenase-digested pancreatic tissue was filtered through a 500 µm polypropylene mesh (Spectrum Laboratories, Rancho Dominguez, Calif.). The resulting acinar units were re-suspended in 20 mL of ALDEFLUOR™ assay buffer (STEMCELL Technologies, Inc.). To label the cells with fluorescent agent, 5 µL of green ALDEFLUOR™ substrate and 5 µL of AldeRed 588-A were used per 1 mL of ALDEFLUOR™ assay buffer. Cell staining proceeded at 37° C. for 50 min. A DEAB control reaction was performed in parallel. Samples were placed in ice to terminate the reaction. Live cell imaging was performed on a Nikon A1 Confocal system (Nikon Instruments, Inc., Melville, N.Y.). The optical configuration was optimized for the DEAB control sample eliminating possible signal in green and red channels. All images were taken using the same optical setting.

Example 2

Syntheses of Representative Aldehyde Dehydrogenase (ALDH) Substrates

Three representative substrates of ALDH containing fluorophores that emit in the red region of the spectrum were synthesized (FIG. 1). Three red fluorophores, (E)-4-(4-(dimethylamino)styryl)-1-(3-isothiocyanatopropyl)pyridin-1-ium chloride 1, BODIPY® 576/589 succinimidyl ester 2, and BODIPY® 650/665 succinimidyl ester 3 were conjugated to aminoacetaldehyde diethyl acetal to produce diethyl acetals 4-6, which were purified by reverse phase liquid chromatography (HPLC) or flash column chromatography.

Maximum excitation and emission wavelengths for 4, 5, and 6 were 493/590 nm, 588/599 nm, and 659/671 nm, respectively (FIG. 2). Acid hydrolysis of the diacetals produced the corresponding aldehydes, AldeRed 493-A, AldeRed 588-A, and AldeRed 659-A.

Example 3

In Vitro Validation of Representative ALDH Substrates

The ALDH specificity of the three representative substrates was tested using human and murine cell lines that express different levels of ALDH, namely, K562 (ALDH$^{hi}$), L1210 (ALDH$^{low}$), and L1210/cpa (ALDH$^{hi}$) (Hilton, 1984). Cell uptake and retention of the substrates were analyzed in the absence and presence of the ALDH inhibitor, diethylaminobenzaldehyde (DEAB) (Jones et al., 1995. As with the original ALDEFLUOR™ reagent, it is the acid-deprotected aldehyde form of the substrate that diffuses into cells and is converted into the corresponding carboxylate by ALDH, which is retained. Substrates were evaluated using the LSR II (BD Biosciences, San Jose, Calif.) fluorescence-activated cell sorter (FACS) equipped with four lasers and 14 emission filters (METHODS and FIGS. 3-5). Of the three compounds tested, AldeRed 588-A demonstrated specific uptake for both K562 and L1210/cpa cells when compared with the DEAB-treated control, indicating ALDH substrate specificity (FIG. 6a). All three substrates diffused into cells as indicated by shifted fluorescent signals in selected emission filter sets compared with non-stained cells (FIGS. 3-5). However, AldeRed 493-A did not demonstrate increased uptake for either ALDH$^{pos}$ cell line, and AldeRed 659-A exhibited only a minimal shift of fluorescent uptake in comparison with DEAB-treated control (FIGS. 3-5, 6a). Without wishing to be bound to any one particular theory, it was reasoned that, despite conversion by ALDH, the hydrophobicity of the carboxylate forms of AldeRed 493-A and AldeRed 659-A would still be too high for them to be trapped within cells. The basic analytical FACS device, FACSCALIBUR™ (BD Biosciences, San Jose, Calif.), with its single blue laser, was used to detect the cellular uptake of AldeRed 588-A using the FL2 filter (FIG. 7). To examine further AldeRed 588-A as a substrate for ALDH, the ability of the ALDEFLUOR™ reagent and AldeRed 588-A for detecting different levels of ALDH expression was compared. L1210 (ALDH$^{low}$) and L1210/cpa (ALDH$^{hi}$) cells were stained and it was found that both reagents were able to differentiate these two cell lines (FIG. 6b). As further confirmation, co-staining with the ALDEFLUOR™ reagent and AldeRed 588-A was performed. Both substrates proportionately co-stained ALDH$^{hi}$ K562 and L1210/cpa cell lines (FIG. 6c). Importantly, these data demonstrate that red fluorescent AldeRed 588-A could be used for co-staining with green fluorophores.

Example 4

Isolation of ALDH$^{hi}$ Human Hematopoietic Stem Cells (HSCs) from Heterogeneous Cord Blood Cells Using AldeRed 588-A Primitive adult stem cells are rare, suggesting that a single-step isolation method would be useful to maximize the efficiency of purification and minimize damage to cells. AldeRed 588-A was tested for its capacity to isolate ALDH$^{hi}$ stem cells from a heterogeneous mixture of cells in human cord blood. Mononuclear cells derived from human cord blood with ALDEFLUOR™ were labeled and the ALDH$^{hi}$ cell population that is not present in cells treated with DEAB (control) was isolated (FIG. 8 a, b). Isolated cells were capable of giving rise to multiple types of differentiated colonies including BFU-E, CFU-G, CFU-M, CFU-GM, and CFU-GEMM (FIGS. 8e, 9) indicating that these ALDH$^{hi}$ cells are enriched HSCs. It was determined whether AldeRed 588-A could perform the same task as ALDEFLUOR™. AldeRed 588-A successfully isolated ALDH$^{hi}$ populations that gave rise to differentiated colonies in a very similar pattern to cells isolated by ALDEFLUOR™ (FIGS. 8e, 9). Human cord blood mononuclear cells were then co-labeled with ALDEFLUOR™ and AldeRed 588-A to determine whether both agents were staining the same HSC populations. It was then confirmed that cells labeled green and red represented identical ALDH$^{hi}$ populations that could be isolated by gating them into their respective channels by FACS (FIG. 8 c, d). In addition, cells exhibited proportional staining patterns for both reagents indicating specificity of the staining (FIG. 10). These results indicate that AldeRed 588-A can efficiently stain and isolate ALDH$^{hi}$ HSCs among heterogeneous cell populations and can be used with green ALDEFLUOR™ to increase the purity of ALDH$^{pos}$ cells, if necessary.

Example 5

Fractionation of ALDH$^{pos}$ Cells from Mice Expressing eGFP

Figure 11A:
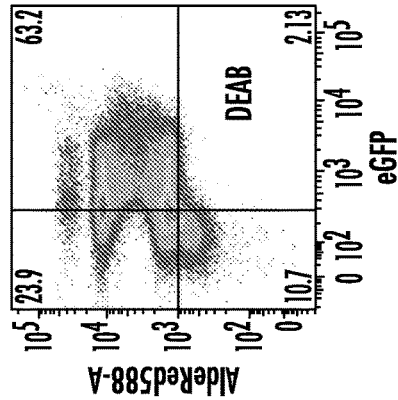
Figure 11B:
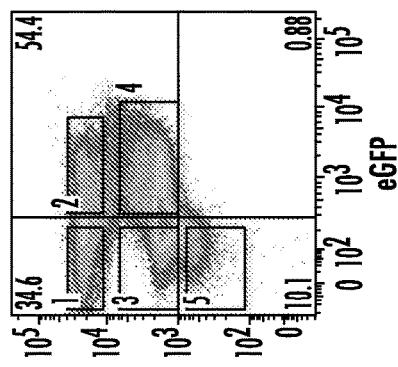
Figure 11C:
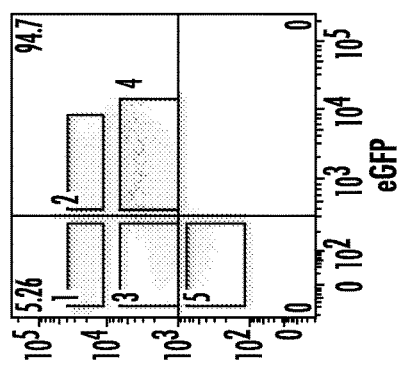
Figure 11D:
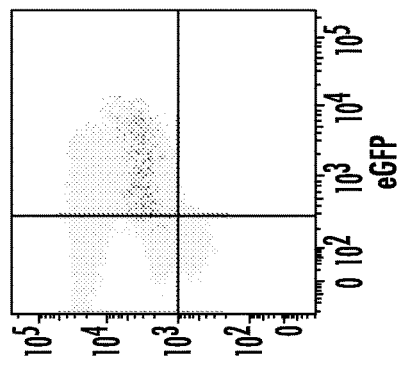
Figure 11E:
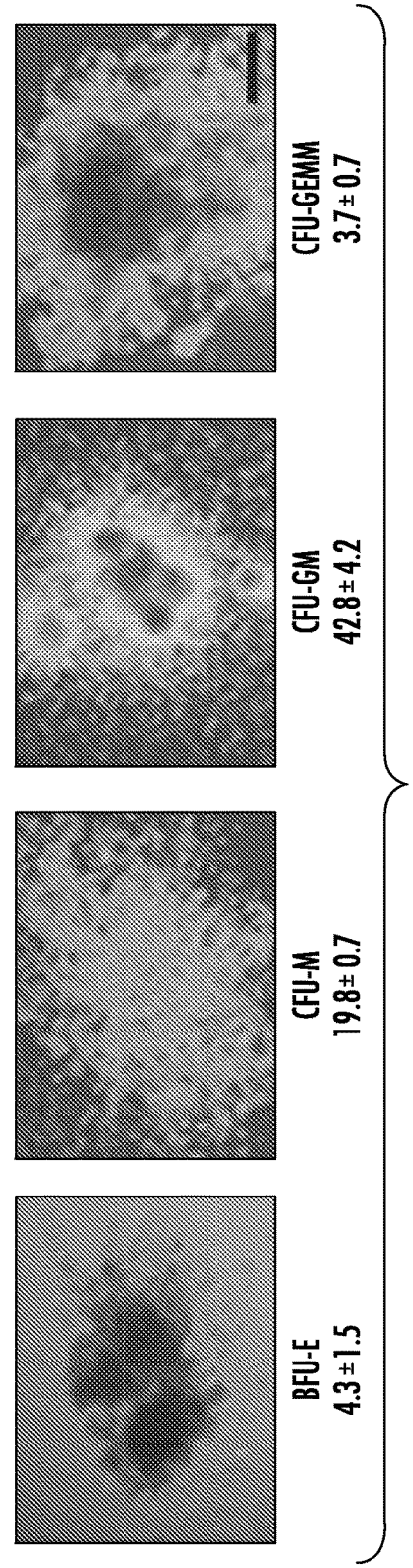

Since the BODIPY® fluorophore for the ALDE-FLUOR™ reagent emits green light, cells harvested from transgenic mice expressing green fluorescent tags cannot be studied with this standard reagent. To test if one could use AldeRed 588-A with cells from a transgenic mouse expressing an enhanced green fluorescent protein (eGFP) tag, enrichment of ALDH$^{int}$ murine hematopoietic stem and progenitor cells (HSPCs) among eGFP-expressing bone marrow (BM) cells isolated from transgenic notch reporter [TNR, Tg(Cp-EGFP)25Gaia] mice was attempted (Duncan et al., 2005). The TNR mice express eGFP in cells with active notch signaling attributed to the C promoter (Cp) binding factor 1 (CBF1) binding site upstream of the eGFP gene. The TNR mice were chosen to be studied for two reasons, both related to biologically relevant systems in which to assess the utility of the AldeRed588-A reagent. First, although it is known that murine HSPCs demonstrate high notch signaling activity (Duncan et al., 2005), the function of notch signaling in maintenance of HSPCs is controversial (Pajcini et al., 2011; Bigas and Espinosa, 2012). Second, there has been disagreement with respect to using ALDH as a marker for murine HSPCs. While the ALDEFLUOR™ reagent has been used to isolate functional murine HSPCs (Pearce and Bonnet, 2007; Armstrong et al., 2004), it has been reported that Aldh1a1 deficient mice had normal hematopoiesis and functional HSPCs (Levi et al., 2009). The TNR mice provide a suitable model to test red fluorescent AldeRed 588-A for its ability to fractionate cells according to ALDH activity from eGFP$^{pos}$ notch active cells. BM cells were isolated from 5- to 6-week old TNR mice and stained with AldeRed 588-A. Those cells were fractionated into 5 different populations: eGFP$^{neg}$/ALDH$^{hi}$ 1, eGFP$^{pos}$/ALDH$^{hi}$ 2, eGFP$^{neg}$/ALDH$^{int}$ 3, eGFP$^{pos}$/ALDH$^{int}$ 4, and eGFP$^{neg}$/ALDH$^{lo}$ 5 (FIG. 11b). To examine in which population HSPCs reside, each population was isolated and colony-forming cell assays were performed. It was found that the eGFP$^{pos}$/ALDH$^{int}$ cell population formed colonies CFU-GEMM, CFU-GM, CFU-M, and BFU-E, while none of the other cell populations formed a single colony (FIG. 11e). To verify that HSPCs reside within the eGFP$^{pos}$/ALDH$^{int}$ population, multi-color FACS analysis was performed for lineage$^-$/c-Kit$^+$/Sca1$^+$ (LKS) HSPCs in addition to ALDH staining using AldeRed 588-A. LKS cells were present within the eGFP$^{pos}$/ALDH$^{int}$ population 4 (FIG. 11c). Additionally, the red fluorescence of the LKS cells shifted when compared with DEAB-treated control, indicating that LKS cells possess active ALDH (FIG. 11d).

Example 6

AldeRed 588-A Stains ALDH$^{pos}$ Murine Pancreatic Centroacinar and Terminal Duct (CA/TD) Cells As an additional example of the utility of AldeRed 588-A, its capacity for identifying ALDH$^{pos}$ cells in vitro with fluorescence microscopy was tested. It was previously shown that a subset of murine pancreatic centroacinar and terminal duct (CA/TD) cells expressing abundant Aldh1a1 and Aldh1a7 can be imaged and isolated using the ALDEFLUOR™ reagent (Rovira et al., 2010). It was also shown that the isolated CA/TD cells exhibited characteristics of murine pancreatic progenitor cells. Using AldeRed 588-A and the ALDEFLUOR™ reagent, isolated murine CA/TD cells were stained and examined under fluorescence microscopy. Both red and green substrates successfully stained CA/TD cells without overlap between the detection filters for each reagent (FIG. 12a, b). Upon co-staining, red and green signals overlapped, indicating ALDH specificity (FIGS. 12c, 13).

Example 7

Discussion

The presently disclosed subject matter provides a red-shifted agent that provides additional flexibility for utilizing ALDH as a marker for stem cell isolation. More particularly, AldeRed 588-A has a red-shifted emission spectrum and possesses physical properties that enable it to function as a probe for ALDH in vivo. The ALDEFLUOR™ assay, the only commercially available method to detect and isolate functionally active ALDH$^{pos}$ cells, depends on differences in fluorescence intensity obtained for the cellular retention of green fluorescent substrate in the presence and absence of the ALDH inhibitor, diethylaminobenzaldehyde (DEAB). As a red-shifted substrate for ALDH, AldeRed 588-A enables isolation of stem cells from a green fluorescent background, which is increasingly prevalent as many genes—including those in transgenic models—are tagged with eGFP. In addition, since many cells demonstrate auto-fluorescence in the green region of the spectrum (Shapiro, 2003), there is a chance of false positive results from stem cell isolation with ALDEFLUOR™. AldeRed 588-A provides an additional way to confirm the purity of ALDH-active cells when used in conjunction with ALDEFLUOR™.

In some embodiments, to act as a functional probe for ALDH, a compound should possess three characteristics: 1) an aldehyde moiety that can serve as a substrate for ALDH; 2) suitable hydrophobicity for free diffusion into cells; and 3) capacity for subsequent trapping within the cytoplasm after conversion of the aldehyde into the corresponding acid by ALDH. Two substrates, AldeRed 493-A and AldeRed 659-A, did not meet those criteria. The degree of trapping is particularly challenging to control, as those two compounds initially stained cells but failed to accumulate. Vaidyanathan et al. reported two radiolabeled ALDH substrates that could be converted into the acid form by the purified enzyme (2009). Both substrates, however, failed to accumulate inside of cells with high ALDH activity when compared with the DEAB control. Without wishing to be bound to any one particular theory, it is believed that the lack of appropriate physical characteristics (hydrophobicity) may be a possible cause.

Cell lines were initially chosen that were known to express abundant, functional ALDH homogeneously for cell-based validation of the representative substrates (FIG. 6). Whether AldeRed 588-A could isolate ALDH$^{hi}$ cells among a mixture of heterogeneous cell populations using mononuclear cells from human cord blood was tested. Human hematopoietic stem cells are known to express high levels of ALDH, and the ALDEFLUOR™ reagent has been used to purify ALDH$^{hi}$ HSCs via simple staining and sorting (Jones et al., 1995; Hess et al., 2004). AldeRed 588-A demonstrated essentially the same efficiency as ALDEFLUOR™ for isolating ALDH$^{pos}$ HSCs and can be used simultaneously (FIGS. 8c-d, 9, 12c, 13). Such co-staining could be used to increase further the specificity of the detection of true ALDH$^{pos}$ cells, particularly in the context of a green fluorescent background.

It has been reported that Aldh1a1 is unnecessary for murine hematopoietic stem and progenitor cell (HSPC) function, but also that Aldh1a1−/− BM cells stain positive with the ALDEFLUOR™ reagent, confusing the issue of ALDH function in HSPCs (Levi et al., 2009). Recently, Garaycoechea et al. demonstrated that murine HSPCs could be stained using ALDEFLUOR™ by virtue of the activity of ALDH2, which plays a role in detoxifying acetaldehyde (Garaycoechea et al., 2012). The presently disclosed results suggest that murine HSPCs possess ALDH activity. It will be interesting to examine whether AldeRed 588-A exhibits a similar staining pattern to ALDEFLUOR™ with respect to HSPCs of Aldh1a1−/− and Aldh2−/− mice. It is anticipated that AldeRed 588-A will provide increased flexibility to study a variety of different aspects of ALDH, particularly in the presence of a green fluorescent background.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Armstrong, L.; Stojkovic, M.; Dimmick, I.; Ahmad, S.; Stojkovic, P.; Hole, N. & Lako, M. Phenotypic characterization of murine primitive hematopoietic progenitor cells isolated on basis of aldehyde dehydrogenase activity. Stem Cells 22, 1142-1151, doi:22/7/1142 [pii]10.1634/stemcells.2004-0170 (2004).

Balber, A. E. Concise review: aldehyde dehydrogenase bright stem and progenitor cell populations from normal tissues: characteristics, activities, and emerging uses in regenerative medicine. Stem Cells 29, 570-575, doi:10.1002/stem.613 (2011).

Bigas, A. & Espinosa, L. Hematopoietic stem cells: to be or Notch to be. Blood 119, 3226-3235, doi:blood-2011-10-355826 [pii]10.1182/blood-2011-10-355826 (2012).

Black, W. J.; Stagos, D.; Marchitti, S. A.; Nebert, D. W.; Tipton, K. F.; Bairoch, A. &Vasiliou, V.,*Human aldehyde dehydrogenase genes: alternatively spliced transcriptional variants and their suggested nomenclature. Pharmacogenet Genomics 19, 893-902, doi:10.1097/FPC.0b013e3283329023 (2009).

Bunting, K. D. ABC transporters as phenotypic markers and functional regulators of stem cells. Stem Cells 20, 11-20 (2002).

Cherry, A. B. C. & Daley, G. Q. Reprogrammed Cells for Disease Modeling and Regenerative Medicine. Annu Rev Med 64, 277-290, doi:DOI 10.1146/annurev-med-050311-163324 (2013).

Duncan, A. W.; Rattis, F. M.; DiMascio, L. N.; Congdon, K. L.; Pazianos, G.; Zhao, C.; Yoon, K.; Cook, J. M.; Willert, K.; Gaiano, N. & Reya, T. Integration of Notch and Wnt signaling in hematopoietic stem cell maintenance. Nat Immunol 6, 314-322, doi:ni1164 [pii]10.1038/ni1164 (2005).

Ebert, A. D., Liang, P. & Wu, J. C. Induced Pluripotent Stem Cells as a Disease Modeling and Drug Screening Platform. J Cardiovasc Pharm 60, 408-416, doi:Doi 10.1097/Fjc.0b013e318247f642 (2012).

Garaycoechea, J. I.; Crossan, G. P.; Langevin, F.; Daly, M.; Arends, M. J. & Patel, K. J. Genotoxic consequences of endogenous aldehydes on mouse haematopoietic stem cell function. Nature 489, 571-575, doi:10.1038/nature11368nature11368 [pii] (2012).

Gerber, J. M.; Smith, B. D.; Ngwang, B.; Zhang, H.; Vala, M. S.; Morsberger, L.; Galkin, S.; Collector, M. I.; Perkins, B.; Levis, M. J.; Griffin, C. A.; Sharkis, S. J.; Borowitz, M. J.; Karp, J. E. & Jones, R. J. A clinically relevant population of leukemic CD34(+)CD38(−) cells in acute myeloid leukemia. Blood 119, 3571-3577, doi:blood-2011-06-364182 [pii]10.1182/blood-2011-06-364182 (2012).

Hassner, A.; Birnbaum, D. & Loew, L. M. Charge-Shift Probes of Membrane-Potential-Synthesis. J Org Chem 49, 2546-2551, doi:Doi 10.1021/Jo00188a006 (1984).

Hess, D. A.; Meyerrose, T. E.; Wirthlin, L.; Craft, T. P.; Herrbrich, P. E.; Creer, M. H. & Nolta, J. A. Functional characterization of highly purified human hematopoietic repopulating cells isolated according to aldehyde dehydrogenase activity. Blood 104, 1648-1655, doi:DOI 10.1182/blood-2004-02-0448 (2004).

Hilton, J. Role of aldehyde dehydrogenase in cyclophosphamide-resistant L1210 leukemia. Cancer Res 44, 5156-5160 (1984).

Inoue, H. & Yamanaka, S. The Use of Induced Pluripotent Stem Cells in Drug Development. Clin Pharmacol Ther 89, 655-661, doi:Doi 10.1038/Clpt.2011.38 (2011).

Jones, R. J.; Barber, J. P.; Vala, M. S.; Collector, M. I.; Kaufmann, S. H.; Ludeman, S. M.; Colvin, O. M. & Hilton, J. Assessment of aldehyde dehydrogenase in viable cells. Blood 85, 2742-2746 (1995).

Levi, B. P., Yilmaz, O. H., Duester, G. & Morrison, S. J. Aldehyde dehydrogenase 1a1 is dispensable for stem cell function in the mouse hematopoietic and nervous systems. Blood 113, 1670-1680, doi:blood-2008-05-156752 [pii] 10.1182/blood-2008-05-156752 (2009).

Ma, I. & Allan, A. L. The role of human aldehyde dehydrogenase in normal and cancer stem cells. Stem Cell Rev 7, 292-306, doi:10.1007/s12015-010-9208-4 (2011).

Marchitti, S. A., Brocker, C., Stagos, D. & Vasiliou, V. Non-P450 aldehyde oxidizing enzymes: the aldehyde dehydrogenase superfamily. Expert Opin Drug Metab Toxicol 4, 697-720, doi:10.1517/17425255.4.6.697 (2008).

Niederreither, K., Subbarayan, V., Dolle, P. & Chambon, P. Embryonic retinoic acid synthesis is essential for early mouse post-implantation development. Nat Genet 21, 444-448, doi:10.1038/7788 (1999).

Pajcini, K. V., Speck, N. A. & Pear, W. S. Notch signaling in mammalian hematopoietic stem cells. Leukemia 25, 1525-1532, doi:10.1038/1eu.2011.1271eu2011127 [pii] (2011).

Pearce, D. J. & Bonnet, D. The combined use of Hoechst efflux ability and aldehyde dehydrogenase activity to identify murine and human hematopoietic stem cells. Exp Hematol 35, 1437-1446, doi:S0301-472X(07)00353-0 [pii] 10.1016/j.exphem.2007.06.002 (2007).

Rovira, M.; Scott, S. G.; Liss, A. S.; Jensen, J.; Thayer, S. P. & Leach, S. D. Isolation and characterization of centroacinar/terminal ductal progenitor cells in adult mouse pancreas. Proc Natl Acad Sci USA 107, 75-80, doi:0912589107 [pii] 10.1073/pnas.0912589107 (2010).

Shapiro, H. M. Practical flow cytometry. 4th edn, (Wiley-Liss, 2003).

Shima, K.; Mizuma, M.; Hayashi, H.; Nakagawa, K.; Okada, T.; Sakata, N.; Omura, N.; Kitamura, Y.; Motoi, F.; Rikiyama, T.; Katayose, Y.; Egawa, S.; Ishii, N.; Horii, A. & Unno, M. Potential utility of eGFP-expressing NOG mice (NOG-EGFP) as a high purity cancer sampling system. J Exp Clin Cancer Res 31, 55, doi:1756-9966-31-55 [pii] 10.1186/1756-9966-31-55 (2012).

Sison-Young, R. L. C.; Kia R.; Heslop, J.; Kelly, L.; Rowe, C.; Cross, M. J.; Kitteringham, N. R.; Hanley, N.; Park, B. K. & Goldring, C. E. Human Pluripotent Stem Cells for Modeling Toxicity. Adv Pharmacol 63, 207-256, doi:Doi 10.1016/B978-0-12-398339-8.00006-9 (2012).

Stevens, A. C.; Frutos, R. P.; Harvey, D. F.; Brian, A. A. Synthesis of protein-reactive (aminostyryl)pyridinium dyes. Bioconj. Chem. 4:19-24 (1993).

Storms, R. W., Trujillo, A. P.: Springer, J. B.: Shah, L.: Colvin, O. M.: Ludeman, S. M.: Smith, C. Isolation of primitive human hematopoietic progenitors on the basis of aldehyde dehydrogenase activity. Proc Natl Acad Sci USA 96, 9118-9123 (1999).

Tiscornia, G., Vivas, E. L. & Belmonte, J. C. I. Diseases in a dish: modeling human genetic disorders using induced pluripotent cells. Nat Med 17, 1570-1576, doi:Doi 10.1038/Nm.2504 (2011).

Vaidyanathan, G.; Song, H., Affleck, D., McDougald, D. L., Storms, R. W.; Zalutsky, M. R. & Chin, B. B. Targeting aldehyde dehydrogenase: a potential approach for cell labeling. Nucl Med Biol 36, 919-929, doi:DOI 10.1016/j.nucmedbio.2009.08.001 (2009).

Vasiliou, V., Pappa, A. & Estey, T. Role of human aldehyde dehydrogenases in endobiotic and xenobiotic metabolism. Drug Metab Rev 36, 279-299, doi:10.1081/DMR-120034001 (2004).

Wuskell, J. P.; Boudreau, D.; Wei, M. D.; Jin, L.; Engl, R.; Chebolu, R.; Bullen, A.; Hoffacker, K. D.; Kerimo, J.; Cohen, L. B.; Zochowski, M. R.; Loew, L. M. Synthesis, spectra, delivery and potentiometric responses of new styryl dyes with extended spectral ranges. J. Neuroscience Methods 151: 200-215 (2006).

Zhang, Y.; Byun, Y.; Ren, Y. R.; Liu, J. O.; Laterra, J.; Pomper, M. G. Identification of inhibitors of ABCG2 by a bioluminescence imaging-based high-throughput assay. Cancer Res. 69(14), 5867-5875 (2009).

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A detectable substrate for aldehyde dehydrogenase (ALDH) comprising a compound having the following structure:

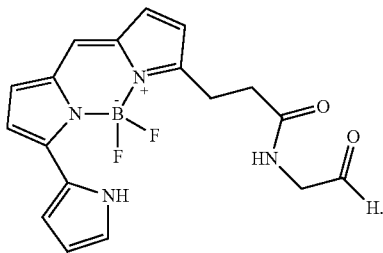

wherein the detectable substrate accumulates in a cell expressing ALDH in an amount sufficient to be detected by fluorescence.

2. A method for distinguishing ALDH-expressing cells in a mixed population of cells, the method comprising:

contacting the mixed population of cells with the detectable ALDH substrate of claim 1;

measuring a fluorescence of the mixed population of cells; and identifying cells exhibiting an increased fluorescence relative to a fluorescence from the mixed population of cells before being contacted with the detectable ALDH substrate.

3. The method of claim 2, wherein measuring the fluorescence is performed by fluorescence microscopy.

4. The method of claim 2, wherein measuring the fluorescence is performed by fluorescence activated cell sorting (FACS).

5. The method of claim 2, wherein at least a portion of the cells in the population express a fluorescent protein.

6. The method of claim 2, wherein the detectable ALDH substrate has a peak emission wavelength that is longer than a peak emission wavelength of a fluorescent protein, if present, by about 30 nm or more.

7. The method of claim 2, wherein the mixed population of cells is contacted with the detectable ALDH substrate in the presence of a multi-drug efflux pump inhibitor having inhibitory action against ATP-binding cassette sub-family B member 1 (ABCB1), ATP-binding cassette sub-family G member 2 (ABCG2), or having dual inhibitory action against both ABCB1 and ABCG2.

8. The method of claim 2, further comprising isolating the identified cells exhibiting increased fluorescence.

9. The method of claim 2, wherein the mixed population of include stem cells.

* * * * *